United States Patent
Catania et al.

(10) Patent No.: US 7,402,559 B2
(45) Date of Patent: *Jul. 22, 2008

(54) COMPOSITION AND METHOD OF TREATMENT FOR UROGENITAL CONDITIONS

(75) Inventors: Anna P. Catania, Milan (IT); James M. Lipton, Woodland Hills, CA (US)

(73) Assignee: MSH Pharma, Incorporated, Los Angeles, CA (US)

( * ) Notice: Subject to any disclaimer, the term of this patent is extended or adjusted under 35 U.S.C. 154(b) by 447 days.

This patent is subject to a terminal disclaimer.

(21) Appl. No.: 10/659,053

(22) Filed: Sep. 8, 2003

(65) Prior Publication Data

US 2005/0037032 A1     Feb. 17, 2005

Related U.S. Application Data

(63) Continuation-in-part of application No. 09/535,066, filed on Mar. 23, 2000, now Pat. No. 6,800,291, application No. 10/659,053, which is a continuation-in-part of application No. 10/442,683, filed on May 21, 2003.

(60) Provisional application No. 60/126,233, filed on Mar. 24, 1999, provisional application No. 60/382,887, filed on May 21, 2002.

(51) Int. Cl.
    A61K 38/08    (2006.01)

(52) U.S. Cl. .............................. 514/2; 514/16; 514/17; 530/328; 530/329

(58) Field of Classification Search ........................ None
See application file for complete search history.

(56) References Cited

U.S. PATENT DOCUMENTS

| | | | |
|---|---|---|---|
| 3,247,182 A | 11/1961 | Schwyzer et al. | |
| 3,300,468 A | 5/1964 | Schwyzer et al. | |
| 4,837,378 A * | 6/1989 | Borgman ..................... | 514/398 |
| 4,918,055 A | 4/1990 | Hruby et al. | |
| 5,028,592 A | 7/1991 | Lipton | |
| 5,157,023 A | 10/1992 | Lipton | |
| 5,739,111 A | 4/1998 | Mahe | |
| 6,001,812 A | 12/1999 | Mahe | |
| 6,800,291 B1 * | 10/2004 | Lipton et al. ............. | 424/278.1 |
| 6,803,044 B1 * | 10/2004 | Catania et al. ............ | 424/278.1 |
| 6,894,028 B2 * | 5/2005 | Lipton et al. .................. | 514/14 |
| 7,115,574 B2 * | 10/2006 | Catania et al. ................. | 514/18 |
| 7,232,804 B2 * | 6/2007 | Lipton et al. ................. | 514/18 |
| 2002/0146374 A | 1/2001 | Lipton | |
| 2002/0183255 A1 | 4/2001 | Lipton et al. | |
| 2002/0137685 A1 | 9/2001 | Catania et al. | |

FOREIGN PATENT DOCUMENTS

| | | |
|---|---|---|
| EP | 0335662 | 10/1989 |
| EP | 0972 522 A1 | 1/2000 |
| FR | 2784028 | 4/2000 |
| JP | 59-021613 | 2/1984 |
| JP | 2-500361 | 2/1990 |
| JP | 06-345665 | 12/1994 |
| JP | 09-124502 | 5/1997 |
| WO | WO87/04623 | 3/1987 |
| WO | 88/00833 | 2/1988 |
| WO | WO93/01211 | 1/1993 |
| WO | WO97/10838 | 3/1997 |
| WO | WO99/58101 | 11/1999 |
| WO | PCT/US00/07846 | 3/2000 |
| WO | WO 00/42856 | 7/2000 |

OTHER PUBLICATIONS

U.S. Appl. No. 09/533,341, filed Mar. 23, 2000, Anna P. Catania et al.
U.S. Appl. No. 09/957,765, filed Sep. 21, 2001, Anna P. Catania et al.
U.S. Appl. No. 60/200,287, filed Apr. 28, 2000, Lipton, J.M.
U.S. Appl. No. 09/774,282, filed Jan. 29, 2001, Lipton, J.M.
U.S. Appl. No. 09/828,272, filed Apr. 6, 2001, Lipton, J.M.
U.S. Appl. No. 09/704,327, filed Nov. 1, 2000, Lipton, J.M.
U.S. Appl. No. 09/535,066, filed Mar. 23, 2000, Lipton et al.
U.S. Appl. No. 10/420,578, filed Apr. 21, 2003, Lipton et al.
U.S. Appl. No. 10/426,647, filed Apr. 29, 2003, Lipton et al.
U.S. Appl. No. 10/298,142, filed Nov. 15, 2002, Lipton.
Airaghi, L., et al., "Elevated concentrations of plasma α-MSH are associated with reduced disease progression in HIV-infected patients," *J. Lab. Clin. Med.* 1333(3) 309-315 (1999).
Airaghi L., et al., "Endogenous cytokine antagonists during myocardial ischemia and thrombolytic therapy." *Am. Heart J.* 130: 204-211, (1995).
Airaghi L., et al., "Plasma concentrations of α-melanocyte-stimulating hormone are elevated in patients on chronic haemodialysis," *Nephrology Dialysis Transplantation* 15:1212-1216, (2000).
Armstrong, "The Microbiology of the Eye." *Ophthal. Physiol. Opt.* 20: 429-503 (2000).
Aylad et al., "Influence of Oral Acyclovir on Ocular Complications of *Herpes zoster ophthalmicus.*" *Eye* 8: 70-74 (1994).
Baker, M., et al., "The Relationship between Interleukin-6 and Herpes Simplex Virus Type-1: Implications for Behavior and Immunopathology," *Brain Behav. Immun.* 13(3):201-11 (1999).
Baker, et al., "Principles of Ambulatory Medicine," *Williams and Wilkins* (1982).

(Continued)

*Primary Examiner*—Anish Gupta
(74) *Attorney, Agent, or Firm*—Gregory M. Zinkl; Dykema Gossett PLLC

(57) ABSTRACT

The present invention is directed to a composition and method for treating uro-genital conditions. One embodiment disclosed is a pharmaceutical composition for use in the treatment of uro-genital conditions wherein said composition comprises a KPV dimer, a first preservative agent, a solvent, an alkalizer, an acrylic acid-based polymer, a second preservative agent and a gelatinizing agent. Another embodiment of the invention is disclosed wherein the composition comprises CKPV (SEQ ID NO: 5) dimer, API, Carbopol®, NF, propylparaben, NF; methylparaben, NF; propylene glycol, USP; edetic acid (EDTA), USP; 2 M sodium hydroxide solution (NaOH); and sterile water for injection, USP. Also disclosed are methods and indications for use of the disclosed composition.

42 Claims, 16 Drawing Sheets

OTHER PUBLICATIONS

Barcellini, W., et al., "Inhibitory Influences of α-MSH peptides on HIV-1 expression in Monocytic cells," *12th World AIDS Conference Geneva*, Abstract No. 60685, Jun. 28-Jul. 3, (1998).

Barcellini W., et al., "α-MSH peptides inhibit HIV-1 expression in chronically infected promonocytic U1 cells and in acutely infected monocytes," *Journal of Leukocyte Biology* 68:693-699, (2000).

Bhattacharya, A., et al., "Effect of Cyclic AMP on RNA and Protein Synthesis in *Candida albicans*," *Biochem, Biophysics. Res. Commun.*, 77: 1438-44 (1977).

Bickers, D., "Sun-Induced Disorders," *Emergency Medicine Clinics of North America*, 3(4): 659-663, 660 (1985).

Capsoni, F., et al., "Effect of Corticosteriods on Neutrophil Function: Inhibition of Antibody-dependent Cell-Mediated Cytotoxicity (ADCC)," *J. Immunopharmacol.* 5, 217-30 (1983).

Cartledge, J.D., et al., "Clinically Significant Azole Cross-Resistance in Candida Isolates from HIV-Positive Patients with Oral Candidosis," *AIDS* 11:1839-44 (1997).

Catania, A., et al., "α-Melanocyte Stimulating Hormone in the Modulation of Host Reactions," *Endocr. Rev.* 14, 564-576 (1993).

Catania, A., et al., "Melanocortin Peptides Inhibit Production of Proinflammatory Cytokines in Blood of HIV-Infected Patients," *Peptides*, 19(6): 1099-1104 (1998).

Catania, A., et al., "The Neuropeptide α-MSH in HIV Infection and Other Disorders in Humans," *Ann. N.Y. Acad. Sci.* 840: 848-856 (1998).

Catania, A., et al., "The Neuropeptide α-MSH has Specific Receptors on Neutrophils and Reduces Chemotaxis in Vitro," *Peptides* 17, 675-679 (1996).

Catania, A., et al., "a-MSH in normal human physiology and disease states," *Trends Endocrinol. Metab.* 11:304-308, (2000).

Catania, A., et al., "a-MSH in systemic inflammation: central and peripheral actions," *Annals of the New York Academy of Sciences*, 885:183-187, (1999).

Catania, A., et al., "Cytokine antagonists in infectious and inflammatory disorders," *Annals of the New York Academy of Sciences* 741: 149-161, (1994).

Catania, A., et al., "α-melanocyte-stimulating hormone peptides in host responses: from basic evidence to human research," *Annals of the New York Academy of Sciences* 680: 412-423, (1993).

Catania, A., et al., "Plasma concentrations and anti-L-cytokine effects of α-melanocyte stimulating hormone in septic patients," *Crit. Care Med.* 28: 1403-1407, (2000).

Catania, A., et al., "Cytokine antagonists in aged subjects and their relation with cellular immunity," *Journal of Gerontology: Biological Sciences* 52A: B93-97, (1997).

Catania, A., et al., "Plasma concentration of cytokine antagonists in patients with HIV infection," *Neuroimmunomodulation* 1: 42-49, (1994).

Catania, A., et al., "Proopiomelanocortin-derived peptides and cytokines: relations in patients with acquired immunodeficiency syndrome," *Clinical Immunology and Immunopathology* 66: 73-79, (1993).

Cavello, J., et al., "Sunburn", *Dermatologic Clinics*, 4(2): 181-187, 181 (1986).

Ceriani, G., et al., "Central Neurogenic Antiinflammatory Action of α-MSH: Modulation of Peripheral Inflammation Induced by Cytokines and other Mediators of Inflammation," *Neuroendocrinology*, 59:138-143 (1994).

Ceriani, G., et al., "The neuropeptide alpha-melanocyte-stimulating hormone inhibits experimental arthritis in rats," *Neuroimunomodulation* 1:28-32, (1994).

Chiao, H., et al., "α-MSH reduces endotoxin-induced liver inflammation," *J. Clin. Invest.* 97: 2038-2044, (1996).

Csata, M., et al., "Enhancement of *Candida albicans* killing activity of separated human epidermal cells by alpha-melanocyte stimulating hormone," *British Journal of Dermatology*, 121(1) 145-147 (1989).

Cutuli, M., et al., "Antimicrobial effects of α-MSH peptides," *Journal of Leukocyte Biology* 67:233-239 (2000).

Deeter, L.B., et al., "Antipyretic Properties of Centrally Administered α-MSH Fragments in the Rabbit," *Peptides* 9, 1285-1288 (1989).

Delgado, R., et al., "Melanocortin peptides inhibit production of proinflammatory cytokines and nitric oxide by activated microglia," *Journal of Leukocyte Biology*, 63: 740-745 (1998).

Domk-Optiz, I., et al., "Stimulation of Macrophages by Endotoxin Results in the Reactivation of a Persistent Herpes Simplex Virus Infection," *Scand J. Immunol.* 32(2):69-75 (1990).

Doughtery et al., "The Role of Tetracycline in Chronic Blepharitis: Inhibition of Lipase Production in *Staphylococcus*." *Inv. Ophthalmol. Vic. Sci.* 32: 2970-2975 (1991).

Eberle, A., et al., "Hormone-Receptor Interactions, The Message Sequence of α-Melanotropin: Demonstration of Two Active Sites," *Clinical Endocrinology* 5, Suppl., 41s-48s (1976).

Eberle, A.N., "The Melanotrophins," *Karger*, Basel, Switzerland (1988).

Fauchere, et al., "Potentiation of the antagonistic effect of ACTH $_{11-24}$ on steroidogenesis by synthesis of covalent dimeric conjugates." *FEBS* 2469, 183(2): 283-286 (1985).

Fauchere, et al., "Synthesis and Antagonistic Activity of Two Covalently Linked Dimers of Adrenocorticotropin-(11–24)-tetradecapeptide." *Helvetica Chimica ACTA* 68: 770-776 (1985).

Fauci, A.S., "Host Factors and the Pathogenesis of HIV-induced Disease," *Nature* 384: 529 (1996).

Feuilloley, et al., Structure-Activity Relationships of Monomeric and Dimeric Synthetic ACTH Fragments in Perifused Frog Adrenal Slices, *J. steroid Biochem* 35(5): 583-592 (1990).

Fitzpatrick, et al., "Acute Effects of Ultraviolet Radiation on the Skin: The Sunburn Reaction," *Dermatology in General Medicine*, 4th Edition, 1651-1655, 1651 (1993).

Fitzpatrick, et al., "Color Atlas and Synopsis of Clinical Dermatology," (1983).

Foster, J., "Sunburn," *eMedicine—Online Medical Reference Textbook*, (last modified May 1, 2000). <http://emedicine.come/emerg/topic798.htm.

Fox, J. A., et.al., "Immunoreactive α-Melanocyte Stimulating Hormone, Its Distribution in the Gastrointestinal Tract of Intact and Hypophysectomized Rats," *Life. Sci.* 28, 2127-2132 (1981).

Galimberti, D., et al., "α-MSH peptides inhibit production of nitric oxide and tumor necrosis factor-a by microglial cells activated with β-amyloid and interferon g.," *Biochemical Biophysical Research Communications* 263: 251-256,(1999).

Getting, et al., "POMC Gene-Derived Peptides Activate Melanocortin Type 3 Receptor on Murine Macrophages, Suppress Cytokin Release, and Inhibit Neutrophil Migration in Acute Experimental Inflammation," *J. Immunol.*, vol. 162, No. 12, pp. 7446-7453 (1999).

Harris, et al., "Alpha-melanocyte stimulating hormone (α-MSH) and melanin-concentrating hormone (MCH) stimulate phagocytosis by head kidney leucocytes of rainbow trout (*Oncorhynchus mykiss*) in vitro," *Fish & Shell Immunol.*, vol. 8, 8:631-638 (1998).

Gow, N.A., "Germ Tube Growth of *Candida albicans*," *Curr. Topics Med. Myco.* 8, 43-55 (1997).

Hart, D.A., et al., "*Staphylococcus aureus* Strains Differ in Their in Vitro Responsiveness to Human Urokinase: Evidence that Methicillin-Resistant Strains are Predominantly Nonresponsive to the Growth-Enhancing Effects of Urokinase," *Can. J. Microbiol.* 42: 1024-31 (1966).

"Harry's Comseticology", *Chemical Publishing*, 7th ed. (1982).

Hiltz, M. E., et al., "Anti-inflammatory Activity of a COOH-terminal Fragment of the Neuropeptide α-MSH," *FASEB J.* 3, 2282-2284 (1989).

Hiltz, M.E., "Anti-inflammatory Activity of α-MSH (11–13) Analogs: Influences of Alterations in Stereochemistry," *Peptides* 12, 767-71 (1991).

Hiltz, M.E., et al., "Alpha-MSH Peptides Inhibit Acute Inflammation and Contact Sensitivity," *Peptides*, 11:979-982 (1990).

Hiltz, M.E., et al., "α-MSH Peptides Inhibit Acute Inflammation Induced in Mice by rIL-1β, rIL-6, rTNF-α and endogenous pyrogen but not that cause by $LTB_4$, PAF and rIL-8," *Cytokine* 4(4):320-328 (1992).

Holdeman, M., et al., "Antipyretic Activity of a Potent α-MSH Analog," *Peptides* 6, 273-5 (1985).

Huang, et al., "Role of central melanocortins in endotoxin-induced anorexia," *Am. J. Physio (Regulatory, Integrative & Comparative Physiology*, vol. 276, No. 3, pp. R864-R871 (1999).

Huberspitz et al., "Corneal Ulceration: An Update from a Specialized Ambulatory Care Centre." *Klinische. Monals. Augen*. 200: 251-256 (1992).

Huh S-K., et al., "The protective effects of α-melanocyte stimulating hormone on canine brain stem ischemia," *Neurosurgery* 40:132-139, (1997).

Ichiyama, T., et al., "Systemically administered a-melanocyte-stimulating hormone peptides inhibit NF-kB activation in experimental brain inflammation," *Brain Research* 836: 31-37, (1999).

Ichiyama, T., et al., "α-Melanocyte-stimulating hormone inhibits NF-κB activation and IκBα degradation in human glioma cells and in experimental brain inflammation," *Experimental Neurology* 157:359-365, (1999).

Ichiyama, T., et al., "Autocrine a-melanocyte-stimulating hormone inhibits NF-κB activation in human glioma cells," *Journal of Neuroscience Research* 58:684-689,(1999).

Ichiyama, T., et al., "NF-kB activation is inhibited in human pulmonary epithelial cells transfected with a-melanocyte-stimulating hormone vector," *Peptides* 21: 1473-1477, (2000).

Ichiyama, T., et al., "Inhibition of peripheral NF-κB activation by central action of α-melanocyte-stimulating hormone," *Journal of Neuroimmunology* 99: 211-217, (1999).

Ishibashi & Kaufman, "The Effects of Subconjunctival Miconozole in the Treatment of Experimental *Candida* Keratitis in Rabbits." *Arch. Ophthalmol*. 103: 1570-1573 (1985).

Khurshid, M.A., et al., "*Staphylococcus aureus* with Reduced Susceptibility to Vancomycin—Illinois, 1999," *Morbidity and Mortality Weekly Report*, 48(51): 1165-1167 (2000), <http://www.cdc.gov/epo/mmwr/preview/mmwrhtml/mm4851a1.htm>.

Lazarus et al., "An in vitro Method Which Assesses Corneal Epithelial Toxicity due to Antineoplastic,Apreservative and Antimicrobial Agents." *Lens Eye Toxic. Res*. 6: 59-85 (1989).

Leeming, "Treatment of Ocular Infections with Topical Antibacterials." *Clin. Pharmacokinet*. 37: 351-360 (1999).

Leibowitz et al., "Human Conjunctivitis: Diagnostic Evaluation." *Arch. Ophthalmol*. 94: 1747-1749 (1976).

Lichtensteiger, W., et al., "Differential Responses of Dopamine Neurons to α-Melanotropin and Analogues in Relation to Their Endocrine and Behavioral Potency," *Life Sci*. 25:2079-2087 (1979).

Lipton, J.M., et.al., "Anti-inflammatory Effects of the Neuropeptide α-MSH in Acute Chronic and Systemic inflammation," *Ann. N.Y. Acad. Sci*. 741, 137-148 (1994).

Lipton, J.M., et al., "Anti-inflammatory Actions of the Neuroimmunomodulator α-MSH," *Immunol. Today* 18, 140-145 (1997).

Lipton, J.M., "Neuropeptide α-Melanocyte-Stimulating Hormone in Control of Fever, the Acute Phase Response, and Inflammation," *Neuroimmune Networks: Physiology and Diseases*, (Alan R. Liss, Inc. 1989) pp. 243-250.

Lipton, J.M., "Modulation of Host Defense by the Neuropeptide α-MSH," *The Yale Journal of Biology and Medicine* 63: 173-182 (1990).

Lipton, J.M., et al., "Marshaling the anti-inflammatory influence of the neuroimmunomodulator α-MSH," *News Physiol. Sci*, 15: 192-195, (2000).

Lipton, J.M., et al., "The neuropeptide α-MSH: a modulator of host reactions," *Seminars in Clinical Immunology* 10: 25-29, (1995).

Lipton, et al., "Mechanisms of antiinflammatory action of the neuro immunomodulatory peptide alpha-MSH," *Annals of the N.Y. Acad. Sci*., vol. 840, pp. 373-380 (1998).

Loetscher, et al., "N-terminal Peptides of Stromal Cell-derived Factor-1 with CXC Chemokine Receptor 4 Agonist and Antagonist Activities." *J. Biological Chem*. 273(35) 22279-22283 (1998).

Lu & Chan, "*Flavobacterium indologenes* Keratitis." *Ophthalmologica* 211: 98-100 (1997).

Luger, T.A., et al., "Production of Immunosuppressing Melanotropins by Human Keratinocytes," *Ann. N.Y. Acad. Sci*. 680: 567-570 (1993).

Lyson, K., et al., "Binding of Anti-Inflammatory α-Melanocyte-Stimulating Hormone Peptides and Proinflammatory Cytokines to Receptors on Melanoma Cells," *Neuroimmunomodulation*, 1:121-126 (1994).

Macaluso, A., et al., "Antiinflammatory Influences of α-MSH molecules: Central Neurogenic and Peripheral Actions," *The Journal of Neuroscience*, 14(4): 2377-2382 (1994).

Mayhall, "Ten Home Remedies for Sunburn," *Seasonal Health*, (Jul. 14, 2000), <http://drkoop.com/wellness/seasonal/summer/sunburn.html>.

Mugridge, K.G., et al., "α-Melanocyte-Stimulating Hormone reduces interleukin-1β effects on rat stomach preparations possibly through interference with type I receptor," *European Journal of Pharmacology*, 197: 151-155 (1991).

Noisakran, S., et al., "Lymphocytes Delay Kinetics of HSV-1 Reactivation from in vitro Explants of Latent Infected Trigeminal Ganglia," *J. Neuroimmunol*. 95(1-2):126-35 (1999).

Patel, A., et al., "Herpes Simplex Virus Type 1 Induction of Persistent NF-κB Nuclear Translocation Increases the Efficiency of Virus Replication," *Virology* 247(2):212-22 (1998).

Potts, "Sunglight, Sunburn, and Sunscreens," *Postgrad. med*., 87:52-61 (1990).

Rajora, N., et.al., "α-MSH Modulates Local and Circulating tumor Necrosis Factor α in Experimental Brain Inflammation," *J. Neurosci*, 17, 2181-2186 (1997).

Rajora, N., et al., "α-MSH Production, Receptors, and Influence on Neopterin, in a Human Monocyte/macrophage Cell Line," *J. Leukoc. Biol*. 59, 248-253 (1996).

Rajora, N., et al., "α-MSH modulates experimental inflammatory bowel disease," *Peptides* 18:381-385, (1997).

"Remington's Pharmaceutical Sciences," *Mack Publishing Co., 18th ed*. (1990).

Richards, D.B., et al., "Effect of a-MSH (11–13) (Lysine-Proline-Valine) on Fever in the Rabbit," *Peptides* 5, 815-817 (1984).

Robbins, S. *Pathologic Basis of Disease 5th ed*., Saunders Co., Philadelphia p. 335-337, 354-355, 1008, 1037-1038. (1994).

Ryan, et al., "Inflammation," a *Scope Publication, The Upjohn Company*, (1977).

Satpathy & Vishalakshi, "Ulcerative Keratitis: Microbial Profile and Sensitivity Pattern: A Five Year Study." *Ann. Ophthalmol. Glaucoma* 27: 301-306 (1995).

Star, R.A., et al., "Evidence of Autocrine Modulation of Macrophage Nitric Oxide Synthase by α-MSH," *Proc. Nat'l. Acad. Sci. (USA)* 92, 8015-8020 (1995).

Stevens, D.L., "Could Nonsteriodal Anti-inflammatory Drugs (NSAIDs) Enhance Progression of Bacterial Infections to Toxic Shock Syndrome?," *Clin. Infect. Dis*. 21, 977-80 (1997).

Szalay, K.S., et al., "Structure-activity studies with ACTH/α-MSH fragments on corticosteroid secretion of isolated zona glomerulosa and fasciculata cells," *Regulatory Peptides*, 11: 187-192 (1985).

Taherzadeh, S., et al., "α-MSH and its receptors in regulation of tumor necrosis factor-a production by human monocyte/macrophages," *Am. J. Physiol*. 276: R1289-R1294, (1999).

Thody, A.J., et.al., "MSH Peptides are Present in Mammalian Skin," *Peptides* 4, 813-815 (1983).

Uehara, Y., et al., "Carboxyl-terminal tripeptide of α-Melanocyte-Stimulating Hormone anagonizes interluekin-1-induced anorexia," *European Journal of Pharmacology*, 220: 119-122 (1992).

Van Nispen, J.W., et al., "Structure-Activity Relationships of Peptides Derived From ACTH, β-LPH and MSH With Regard To Avoidance Behavior in Rats," *Pharmac. Ther*. 16: 67-102 (1982).

Walev, I., et.al., "Enhancement by TNF-alpha of Reactivation and Replication of Latent Herpes Simplex Virus from Trigeminal Ganglia of Mice," *Arch Virol*. 140(6):987-92 (1995).

Watanabe, T., et al., "Inhibition of IL-1β-induced peripheral inflammation by peripheral and central administration of analogs of the neuropeptide α-MSH," *Brain Research Bulletin* 32: 311-314, (1993).

Weiss, et al., "Corticotropin-peptide regulation of intracellular cyclic-AMP production in cortical neurons in primary culture," *J. Neurochem*. vol. 45, No. 3, pp. 869-874 (1985).

Wenzel, R.P., et al., "Candida Species: Emerging Hospital Bloodstream Pathogens," *Infect. Control. Hosp. Epidemiol.* 12: 523-4 (1991).

Wilkins et al., "Penicillin-Resistant *Streptococcus pneumoniae* Keratitis," *Cornea* 15: 99-100 (1996).

Wong, K.Y., et al., "A Potential Mechanism of Local Anti-inflammatory Action of Alpha-Melanocyte-Stimulating Hormone within the Brain: Modulation of Tumor Necrosis Factor-Alpha Production by Human Astrocytic Cells," *Neuroimmunomodulation*, 4:37-41 (1997).

"Vaginitis," *National Institute of Child Health and Human Development—Publications On-line* (last modified Jan. 12, 2000). <www.nichd.nih.gov/publications/pubs;/vagtoc.html>.

"Tampons and Asbestos, Dioxins, & Toxic Shock Syndrome," *FDA Center for Devices and Radiological Health* (Jul. 23, 1999), <http://www.fda.gov/cdrh/ocd/tamponsabs.html>.

"Women's Health, Urinary Tract Infections: A Patient's Guide to Treatment," *AMA Health Insight, On-Line Health Information for Everyone* (last updated Oct. 30, 1998) <http://www.ama-assn.org/insight/h_focus/worn_hlth/uti/uti.htm>.

Lipton, J.M., "The Neuropeptide Alpha-Melanocyte-Stimulating Hormore Inhibits Experimental Arthritis in Rats," *Neuroimmunomodulation* 1:28-32 (1994).

Manna S.K. et al., Journal of Immunology, 1998, vol. 161, No. 6, pp. 2873-2880.

Skerlavaj et al., "Biological Characterization of Two Novel Cathelicidin-Derived Peptides and Identification of Structural Requirements for Their Antimicrobial and Cell Lytic Activities," J. Biol. Chem., 1996, 271, 28375-81.

Shiels et al., "Selection of Diversity at Putative Glycosylation Sites in the Immunodominant Merozite/Piroplasm Surface Antigen of Theileria Parasites," Mol. Biochem, Parasit. 1995, 72, 149-162.

\* cited by examiner

Influence of α-MSH peptides on *C. albicans* germ tube formation.
A) blastospores;
B) horse serum-induced germ tube formation;
C) effect of α-MSH (1-13) treatement on germ tube formation
D) effect of α-MSH (11-3) treatement on germ tube formation

```
                        SEQUENCE LISTING

<160> NUMBER OF SEQ ID NOS: 15

<210> SEQ ID NO 1
<211> LENGTH: 3
<212> TYPE: PRT
<213> ORGANISM: Artificial Sequence
<220> FEATURE:
<223> OTHER INFORMATION: Designed polypeptide with anti-inflammatory,
      anti-microbial, anti-fungal, and anti-viral properties.

<400> SEQUENCE: 1

Lys Pro Val
1

<210> SEQ ID NO 2
<211> LENGTH: 7
<212> TYPE: PRT
<213> ORGANISM: Artificial Sequence
<220> FEATURE:
<223> OTHER INFORMATION: Designed polypeptide with anti-inflammatory,
      anti-microbial, anti-fungal, and anti-viral properties.

<400> SEQUENCE: 2

Met Glu His Phe Arg Trp Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Designed polypeptide with anti-inflammatory,
      anti-microbial, anti-fungal, and anti-viral properties.

<400> SEQUENCE: 3

His Phe Arg Trp Gly Lys Pro Val
1               5

<210> SEQ ID NO 4
<211> LENGTH: 13
<212> TYPE: PRT
<213> ORGANISM: Homo sapiens
<220> FEATURE:
<223> OTHER INFORMATION: Designed polypeptide with anti-inflammatory,
      anti-microbial, anti-fungal, and anti-viral properties/naturally
      occurring peptide.

<400> SEQUENCE: 4

Ser Tyr Ser Met Glu His Phe Arg Trp Gly Lys Pro Val
1               5                   10

<210> SEQ ID NO 5
<211> LENGTH: 4
<212> TYPE: PRT
<213> ORGANISM: Artificial Sequence
<220> FEATURE:
<223> OTHER INFORMATION: Designed polypeptide with anti-inflammatory,
      anti-microbial, anti-fungal, and anti-viral properties.

<400> SEQUENCE: 5
```

```
Cys Lys Pro Val
 1

<210> SEQ ID NO 6
<211> LENGTH: 5
<212> TYPE: PRT
<213> ORGANISM: Artificial Sequence
<220> FEATURE:
<223> OTHER INFORMATION: C-terminal sequences of alpha-MSH/Cys is DCys.

<400> SEQUENCE: 6

Trp Cys Lys Pro Val
 1               5

<210> SEQ ID NO 7
<211> LENGTH: 6
<212> TYPE: PRT
<213> ORGANISM: Artificial Sequence
<220> FEATURE:
<223> OTHER INFORMATION: Designed polypeptide with anti-inflammatory,
      anti-microbial, anti-fungal, and anti-viral properties/Cys is
      hCys.

<400> SEQUENCE: 7

Arg Trp Cys Lys Pro Val
 1               5

<210> SEQ ID NO 8
<211> LENGTH: 4
<212> TYPE: PRT
<213> ORGANISM: Artificial Sequence
<220> FEATURE:
<223> OTHER INFORMATION: Designed pollypeptide with anti-inflammatory,
      anti-microbial, anti-fungal, and anti-viral properties/Cys is
      DhCys.

<400> SEQUENCE: 8

Cys Lys Pro Val
 1

<210> SEQ ID NO 9
<211> LENGTH: 39
<212> TYPE: PRT
<213> ORGANISM: Homo sapiens
<220> FEATURE:
<223> OTHER INFORMATION: Designed polypeptide with anti-inflammatory,
      anti-microbial, anti-fungal, and anti-viral properties/naturally
      occurring peptide.

<400> SEQUENCE: 9

Ser Tyr Ser Met Glu His Phe Arg Trp Gly Lys Pro Val Gly Lys Lys
 1               5                  10                  15

Arg Arg Pro Val Lys Val Tyr Pro Ala Gly Glu Asp Asp Glu Ala Ser
                20                  25                  30

Glu Ala Phe Pro Leu Glu Phe
            35

<210> SEQ ID NO 10
<211> LENGTH: 22
<212> TYPE: PRT
<213> ORGANISM: Artificial Sequence
<220> FEATURE:
<223> OTHER INFORMATION: Designed polypeptide with anti-inflammatory,
      anti-microbial, anti-fungal, and anti-viral properties.

<400> SEQUENCE: 10

Arg Pro Val Lys Val Tyr Pro Ala Gly Glu Asp Asp Glu Ala Ser Glu
```

```
                1               5              10              15

Ala Phe Pro Leu Glu Phe
            20

<210> SEQ ID NO 11
<211> LENGTH: 35
<212> TYPE: DNA
<213> ORGANISM: Artificial sequence
<220> FEATURE:
<223> OTHER INFORMATION: Oligonucleotide probes for NF-kB.

<400> SEQUENCE: 11 gat cca agg gga ctt tcc gct ggg gac ttt cca tg                          35

<210> SEQ ID NO 12
<211> LENGTH: 35
<212> TYPE: DNA
<213> ORGANISM: Artificial sequence
<220> FEATURE:
<223> OTHER INFORMATION: Oligonucleotide probes for NF-kB.

<400> SEQUENCE: 12 gat cca tgg aaa gtc ccc agc gga aac tcc cct tg                          35

<210> SEQ ID NO 13
<211> LENGTH: 4
<212> TYPE: PRT
<213> ORGANISM: Artificial sequence
<220> FEATURE:
<223> OTHER INFORMATION: Designed pollypeptide with anti-inflammatory,
      anti-microbial, anti-fungal, and anti-viral properties.

<400> SEQUENCE: 13

Gly Lys Pro Val
1

<210> SEQ ID NO 14
<211> LENGTH: 5
<212> TYPE: PRT
<213> ORGANISM: Artificial sequence
<220> FEATURE:
<223> OTHER INFORMATION: Designed polypeptide with anti-inflammatory,
      anti-microbial, anti-fungal, and anti-viral properties.

<400> SEQUENCE: 14

Trp Gly Lys Pro Val
1               5

<210> SEQ ID NO 15
<211> LENGTH: 6
<212> TYPE: PRT
<213> ORGANISM: Artificial sequence
<220> FEATURE:
<223> OTHER INFORMATION: Designed polypeptide with anti-inflammatory,
      anti-microbial, anti-fungal, and anti-viral properties.

<400> SEQUENCE: 15

Arg Trp Gly Lys Pro Val
1               5
```

COMPOSITION AND METHOD OF TREATMENT FOR UROGENITAL CONDITIONS

CROSS-REFERENCE TO RELATED APPLICATIONS

The present application is a Continuation-in-Part of U.S. patent application Ser. No. 09/535,066, filed Mar. 23, 2000 now U.S. Pat. No. 6,800,291, which claims priority to U.S. Provisional Application Ser. No. 60/126,233, filed Mar. 24, 1999. The present application is also a Continuation-in-Part of U.S. patent application Ser. No. 10/442,683 filed May 21, 2003, which claims priority to U.S. Provisional Application Ser. No. 60/382,887, filed May 21, 2002, all of which are fully incorporated by reference, including drawings, as if fully set forth herein.

TECHNICAL FIELD OF INVENTION

The present invention relates to the field of treatment for urogenital conditions.

BACKGROUND OF THE INVENTION

Uro-genital conditions or diseases commonly affect both men and women. These conditions include infections and/or inflammation of the urinary system and the genital system. For example, according to the National Institute of Child Health and Human Development (NICHD), "most women will have at least one form of vaginitis in their lifetime." *Vaginitis, National Institute of Child Health and Human Development—Publications On-line*, www.nichd.nih.giv/publications/pubs/vag1.htm. The causes for vaginitis range from bacterial, fungal or viral infections to irritations from chemicals in creams, sprays, or even clothing that are in contact with this area. Id. For women with bacterial and fungal infections, these infectious agents often originate from the rectal area and migrate across the perineum to reach the vagina or the urethra.

A common type of vaginitis is candidiasis or yeast infection that is most commonly caused by *Candida albicans*. The *Candida* species are part of an individual's normal flora of microbial organisms present in skin, mouth, and the gastrointestinal tract. *Robbins Pathologic Basis of Disease* 5$^{th}$ ed., Saunders Co., Philadelphia (1994) p. 354. They also live in small numbers in a woman's vagina. They grow best in warm, moist surfaces such as the vagina or the oral cavity. They are normally non-pathogenic, but when a change in their environment occurs, such as in response to a woman's hormonal changes in menopause, pregnancy, or in response to stress, they can overgrow to cause a yeast infection. These changes can also occur in immunosuppressed or compromised individuals such as people undergoing chemotherapy, taking immunosuppresants, or afflicted with AIDS.

Current treatment for candidiasis includes over the counter drugs with active ingredients such as butoconazole nitrate (Femstat®), clotrimazole (Gyne-Lotrimin® and others), miconazole (Monistat® and others), and tioconazole (Vagistat®). These drugs are topically applied in the vagina and break down *Candida*'s cell wall. Other similar treatments include prescription drugs with active ingredients in the same family such as fluconazole (Diflucan®), terconazole (Terazol®), and ketoconazole (Nizoral®).

Although vaginitis has been commonly associated with *Candida*, bacterial vaginosis is actually the most common vaginal infection in women of reproductive age according to the NICHD. *Vaginitis*, supra. Overgrowing of bacteria in the vagina causes bacterial vaginosis much like *Candida*, but the drugs used for its treatment are different.

On the other hand, men can also contract *Candida* infections on their penis involving the glans and the prepuce. Balanoposthitis, a nonspecific infection of the glans and prepuce, is caused by a wide variety of organisms including fungi such as *Candida* and pyogenic bacteria such as *Staphylococci* Sp. *Robbins Pathologic Basis of Disease* 5$^{th}$ ed., Saunders Co., Philadelphia (1994), p. 1008.

*Staphylococci* are gram positive bacteria that are normally present in skin and other mucosal membranes of the body. *Staphylococcus aureus*, in particular, is a virulent pathogen that causes a myriad of conditions and diseases stemming from skin lesions, endocarditis, respiratory infection, food poisoning and toxic shock syndrome.

For women using highly absorbent tampons, it is known that *S. aureus* can colonize the vagina and secrete a toxin called toxic shock syndrome toxin (TSST-1). According to the Food and Drug Administration, approximately half of the toxic shock syndrome cases reported today are associated with tampon use during menstruation and usually in young women. *Tampons and Asbestos, Dioxin, & Toxic Shock Syndrome, FDA Center for Devices and Radiological Health* (Jul. 23, 1999), www.fda.gov/cdrh/ocd/tamponsabs.html.

*S. aureus* infections are commonly treated with methicillin. Although it is very effective, some strains of *S. aureus* have developed resistance to methicillin, and only a few antibiotics can successfully treat methicillin-resistant *Staphylococcus aureus* (MRSA) infections. One of these antibiotics commonly used for MRSA is vancomycin. A strain of *S. aureus*, however, with reduced susceptibility to vancomycin (VISA) has already been identified. Khurshid, M. A., et. al., *Staphylococcus aureus with Reduced Susceptibility to Vancomycin—Illinois*, 1999, *Morbidity and Mortality Weekly Report*, 48(51): 1165-1167 (2000), www.cdc.gov/epo/mmwr/preview/mmwrhtml/mm4851a1.htm. The emergence of antibiotic resistant bacterial strains has created a need for alternative ways to combat bacterial infections.

In addition to infection by fungi and bacteria, viral vaginitis is also common. These infections are most often transmitted through sexual intercourse. Viral vaginitis includes infection by herpes simplex virus (HSV) or human papillomavirus (HPV). HSV viruses, for example, replicate in the genital area, which is the site of entrance, and also infect the neurons that innervate the genitals. To avoid the body's immune system, HSV viruses can remain latent in these neurons, and become reactivated in response to environmental conditions such as stress, immunosuppression, irradiation, or viral infection. Current treatments for HSV include drugs such as acyclovir, famciclovir, or valacyclovir.

As for the urinary system, according to the American Medical Association, urinary tract infections (UTIs) are one of the most common disorders prompting a physician visit. *Women's Health, Urinary Tract Infections: A Patient's Guide to Treatment, AMA Health Insight, On-Line Health Information for Everyone*, www.ama-assn.org/insight/h_focus/wom_hlth/uti/uti.htm. These infections are most often caused by *Escherichia coli*, but can also involve organisms such as *Candida* Sp. and *Staphylococci* Sp. Id. These infections can start at the urethra and travel up to the bladder causing cystitis. Ultimately, it can even ascend to the kidneys through the ureters and cause pyelonephritis. Both men's and women's urinary systems can become infected with these microorganisms.

Since uro-genital conditions are not confined to one single cause, current treatments require different drugs to treat specific causes. These causes have to be first identified. Identification requires time, but more so, requires a gynecological examination for women to determine the specific infectious agents or lack thereof.

With the increased use of antibiotics and other drugs, microorganisms, such as methicillin-resistant *Staphylococcus aureus*, are increasingly developing resistance to currently available drugs. Thus, a continuing need exists for new classes of drugs that can combat the broad spectrum of infectious agents. It has been discovered that dimers comprising Lysine-Proline-Valine as well as other alpha-MSH based peptides disclosed herein, are effective in treating urogenital conditions.

SUMMARY OF THE INVENTION

The present invention is directed to a system for treating uro-genital conditions. One aspect of this invention involves a treatment comprising one or more polypeptides with an amino acid sequence including KPV (SEQ ID NO: 1), MEHFRWG (SEQ ID NO: 2), HFRWGKPV (SEQ ID NO: 3), VPKC (SEQ ID NO: 5) -s-s CKPV (SEQ ID NO: 5) or SYSMEHFRWGKPV (SEQ ID NO: 4) for treatment of urogenital conditions. VPKC-s-s-CKPV is an example of a "KPV dimer" wherein a disulfide bond exists between N-terminal cysteines of each monomer. Hereon in this disclosure, "CKPV dimer" will be the term used to identify this form of a KPV dimer, i.e., two CKPV monomers linked through a disulfide bond, i.e., VPKC (SEQ ID NO: 5) -s-s-CKPV (SEQ ID NO: 5). It is contemplated that other KPV dimers may be used in the disclosed composition.

IN THE DETAILED DESCRIPTION OF THE PREFERRED EMBODIMENTS

Uro-genital conditions can include infections, inflammation, or both. In one preferred embodiment of the invention, the uro-genital condition includes infection and/or inflammation of the vagina, vulva, urinary tract, penis, and/or the rectum. In another preferred embodiment of the invention, the one or more polypeptides are dissolved in a carrier. In another preferred embodiment of the invention, the one or more polypeptides are associated with a tampon for preventing toxic shock syndrome. In another preferred embodiment, the one or more polypeptides are associated with a contraceptive for prevention of sexually transmitted diseases or infections. In another preferred embodiment, the one or more polypeptides are associated with a suppository for insertion into the vagina or rectum. In another preferred embodiment of the invention, the one or more polypeptides are dissolved in a liquid carrier for douching the vagina.

In one aspect of the invention, a pharmaceutical composition is disclosed for use in the treatment of urogenital conditions comprising a KPV dimer, preservative agents, a solvent, an alkalizer, an acrylic acid based polymer, and a gelatinizing agent.

In another aspect of the invention, a pharmaceutical composition for use in the treatment of uro-genital conditions comprises an acrylic acid-based polymer, for example, CARBOPOL®, National Formulary (hereon NF); propylparaben, NF; methylparaben, NF; propylene glycol, United States Pharmacopeia (hereon USP); edetic acid (hereon EDTA), USP; the CKPV dimer, (which is also identified by the Trademark "CZEN002™"), Active Pharmaceutical Ingredient (hereon API); 2 M sodium hydroxide solution (hereon NaOH); and sterile water for injection, USP. It is contemplated that certain ingredients listed may be modified, replaced or eliminated.

DETAILED DESCRIPTION OF THE PREFERRED EMBODIMENTS

Figure 1:
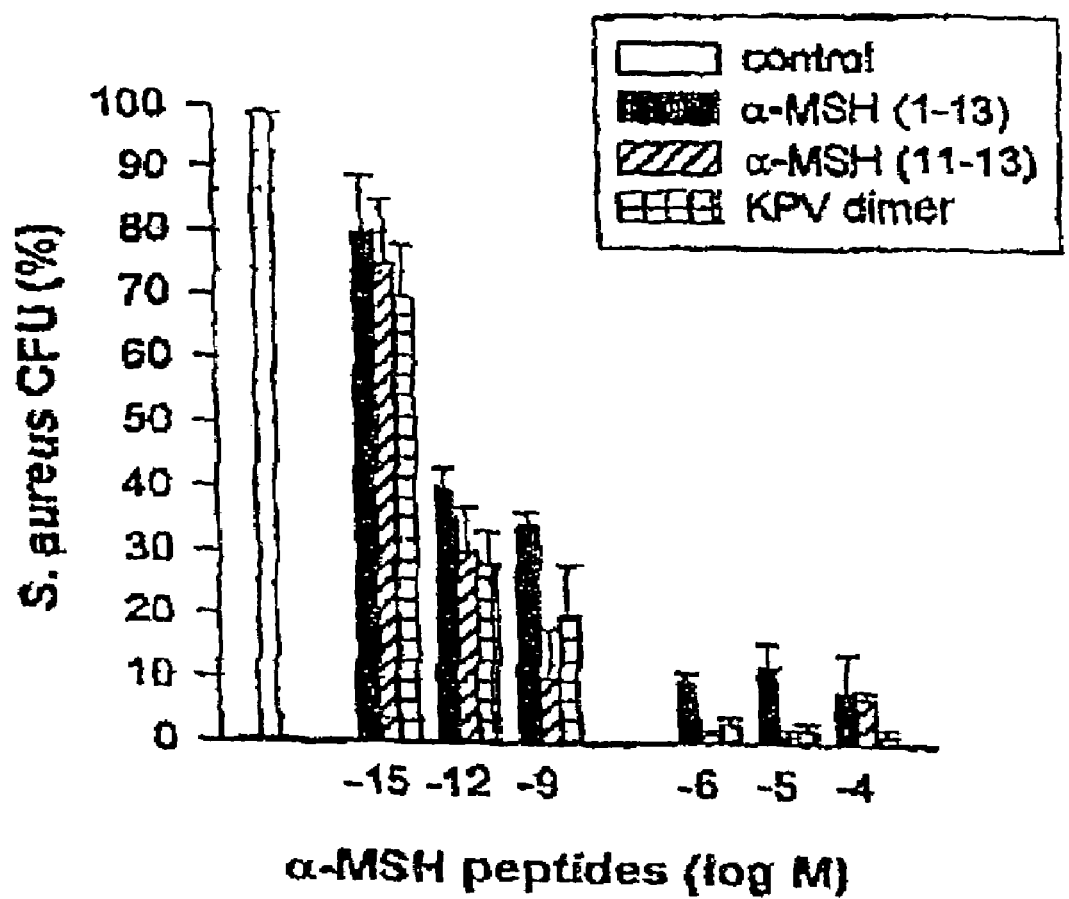
FIG. 1 shows the inhibitory effects of alpha-MSH peptides on the growth of *S. aureus*.

The references cited below are hereby incorporated by reference as if fully set forth herein. The present invention involves composition and method for treating uro-genital conditions with the use of alpha-melanocyte stimulating hormone ("alpha-MSH") peptides and dimers thereof. Alpha-MSH is an ancient thirteen amino-acid peptide (SEQ ID NO: 4) produced by post-translational processing of the larger precursor molecule propiomelanocortin. It shares the 1-13 amino acid sequence with adrenocorticotropic hormone ("ACTH"), also derived from propiomelanocortin. Alpha-MSH is known to be secreted by many cell types including pituitary cells, monocytes, melanocytes, and keratinocytes. It can be found in the skin of rats, in the human epidermis, or in the mucosal barrier of the gastrointestinal tract in intact and hypophysectomized rats. See, e.g., Eberle, A. N., *The Melanotrophins*, Karger, Basel, Switzerland (1998); Lipton, J. M., et. al., *Anti-inflammatory Influence of the Neuroimmunomodulator alpha-MSH*, Immunol. Today 18, 140-145 (1997); Thody, A. J., et. al., *MSH Peptides are Present in Mammalian Skin*, Peptides 4, 813-815 (1983); Fox, J. A., et. al., *Immunoreactive a-Melanocyte Stimulating Hormone, Its Distribution in the Gastrointestinal Tract of Intact and Hypophysectomized Rats*, Life. Sci. 18, 2127-2132 (1981).

Alpha-MSH peptides are known to have potent antipyretic and anti-inflammatory properties, yet they have extremely low toxicity. They can reduce production of host cells' proinflammatory mediators in vitro, and can also reduce production of local and systemic reactions in animal models for inflammation. The "core" alpha-MSH sequence (4-10) (SEQ ID NO: 2), for example, has learning and memory behavioral effects but little antipyretic and anti-inflammatory activity. In contrast, the active message sequence for the antipyretic and anti-inflammatory activities reside in the C-terminal amino-acid sequence of alpha-MSH, that is, Lysine-Proline-Valine ("Lys-Pro-Val" or "KPV") (SEQ ID NO: 1). This tripeptide has activities in vitro and in vivo that parallel those of the parent molecule. The anti-inflammatory activity of alpha-MSH peptides are disclosed in the following two patents, which are hereby incorporated by reference: U.S. Pat. No. 5,028,592, issued on Jul. 2, 1991 to Lipton, J. M., entitled Antipyretic and Anti-inflammatory Lys Pro Val Compositions and Method of Use; U.S. Pat. No. 5,157,023, issued on Oct. 20, 1992 to Lipton, J. M., entitled Antipyretic and Anti-inflammatory Lys Pro Val Compositions and Method of Use; see also Catania, A., et. al., α-*Melanocyte Stimulating Hormone in the Modulation of Host Reactions, Endocr. Rev.* 14, 564-576 (1993); Lipton, J. M., et. al., *Anti-inflammatory Influence of the Neuroimmunomodulator alpha-MSH, Immunol. Today* 18, 140-145 (1997); Rajora, N., et. al., *alpha-MSH Production Receptors and Influence on Neopterin, in a Human Monocyte/macrophage Cell Line, J. Leukoc. Biol.* 59, 248-253 (1996); Star, R. A., et. al., *Evidence of Autocrine Modulation of Macrophage Nitric Oxide Synthase by alpha-MSH, Proc. Nat'l. Acad. Sci.* (*USA*) 92, 8015-8020 (1995); Lipton, J. M., et. al., *Anti-inflammatory Effects of the Neuropeptide alpha-MSH in Acute Chronic and Systemic inflammation, Ann. N.Y. Acad. Sci.* 741, 137-148 (1994); Fajora, N., et. al., *alpha-MSH Modulates Local and Circulating Tumor Necrosis Factor* α *in Experimental Brain Inflammation, J. Neuroosci,* 17, 2181-2186 (1995); Richards, D. B., et. al., *Effect of a-MSH* (11-13) (*lysine-proline-valine*) *on Fever in the Rabbit, Peptides* 5, 815-817 (1984); Hiltz, M. E., et. al., *Anti-inflammatory Activity of a COOH-terminal Fragment of the Neuropeptide alpha-MSH, FASEB J.* 3, 2282-2284 (1989).

In addition to its anti-inflammatory and anti-pyretic function, one aspect of the present invention involves the antimicrobial or anti-infection activity of alpha-MSH peptides. As described below, alpha-MSH peptides have significant anti-infection uses, including, for example, use in reducing the viability of microbes, reducing the germination of yeast, killing microbes without reducing the killing of microbes by human neutrophils, for treating inflammation associated with microbial infection without reducing microbial killing, increasing the accumulation of cAMP in microbes, and inhibiting the replication and expression of viral pathogens.

In a preferred embodiment of the invention, these antimicrobial or anti-infection activities are most particularly associated with the C-terminal amino-acid sequence—KPV (SEQ ID NO: 1). This tripeptide, along with its dimers and other alpha-MSH peptides, are effective over a very broad range of concentrations, including picomolar concentrations that normally occur in human plasma. Nanomolar and micromolar concentrations yield more potent concentrations.

As discussed in the background section, uro-genital conditions are not confined to one single cause. Multiple organisms and infectious agents, from bacteria and fungi to viruses, individually or in combination, can cause a wide variety of conditions including vaginitis, vulvitis, urethritis, balanophosthithis, candidiasis, sexually transmitted diseases, and toxic shock syndrome. For treatment of these conditions, alpha-MSH peptides can be applied locally to the site of the infection and/or inflammation by methods known in the art. For example, alpha-MSH peptides can be dissolved in solutions such as phosphate buffer saline, hyalurinate, methylcellulose, carboxymethlcellulose, or ethanol. Common carriers such as ointment, cream, gel, dissolvable pill, aerosol spray, suppository, liquid solution for douche or the absorbent material of tampons can carry alpha-MSH peptides as active ingredients for treating uro-genital conditions. These carriers can be applied to the site of the infection or inflammation by an applicator such as syringes or syringe-like apparatus, bandages, catheters, tubes with a plunger, spatula or other types of flat surface applicators, condoms, sponges, diaphragms, tampon applicators or fingers.

More specifically, one preferred embodiment of the invention is to dissolve alpha-MSH peptides in a liquid-based carrier. This carrier carrying the solvated alpha-MSH peptides is then stored in a pressurized canister. Upon release of the carrier by a release valve or other mechanisms from the pressurized canister, an aerosol foam is formed and captured into a syringe or a syringe-type apparatus. The syringe is then partially inserted into the vagina and its contents delivered into the vaginal canal. The syringe or syringe-type apparatus and its opening can also be molded to different size, shapes, and lengths to accommodate insertion into different uro-genital areas such as the urethra and may also be used in the rectum.

Another preferred embodiment of the invention is a suppository that comprises a carrier. This carrier, such as a gel or glycerin, is solid or semi-solid at room temperature, but melts at body temperature when inserted into the vagina or rectum. This carrier carrying the solvated alpha-MSH peptides are delivered into the site of uro-genital condition when the carrier melts.

Delivering alpha-MSH peptides to the outside area of the uro-genital area such as the vulva or the glans and prepuce of the penis can be achieved by topically applying a cream, ointment, gel, spray, foam, or balm, the compositions of which are already well known in the art.

In another aspect of the invention, tampons can be treated with alpha-MSH peptides during the manufacturing process. The presence of alpha-MSH in tampons may inhibit the growth of microorganisms such as *Staphylococcus aureus* that secretes the toxic shock syndrome toxin (TSST-1). The processes for making tampons are already well known in the art. Treatment of the tampon's absorbent material with alpha-MSH or its derivatives may be accomplished by first soaking the absorbent material in a solution of alpha-MSH peptides. The absorbent material can then be allowed to dry. Alternatively, alpha-MSH may be sprinkled onto the tampon's absorbent material as dry powder.

In another aspect of the invention, alpha-MSH peptides may be delivered to the site of the infection by using contraceptives such as condoms, diaphragms, sponges, or other barrier-type mechanisms used for preventing pregnancy or sexually transmitted diseases. Alpha-MSH peptides can be dissolved in the lubricant used in condoms, in the gel or foam used together with the diaphragms, or in any other spermicidal solution used in conjunction with condoms, diaphragms, or sponges.

In another aspect of the invention, alpha-MSH peptides may be dissolved in a liquid for use with a douche. The liquid can be delivered by the douche into the vagina for treating infection and/or inflammation.

In another aspect of the invention, a pharmaceutical composition for use in the treatment of urogenital conditions comprises a CKPV dimer (SEQ ID NO: 5). preservative agents, a solvent, an alkalizer, CARBOPOL®, and a gelatinizing agent. The composition may further comprise a chelating agent. These ingredients may be modified, replaced or eliminated. A CKPV dimer (SEQ ID NO: 5) is preferred over other useful alpha-MSH peptides as it has been shown to be more efficacious in treating vaginitis. See, Example XII below.

In another aspect of the invention, a pharmaceutical composition is disclosed for use in the treatment of uro-genital conditions wherein said composition comprises an acrylic acid-based polymer, for example. CARBOPOL®, NF; propylparaben, NF; methylparaben, NF; propylene glycol, USP; EDTA, USP; CKPV (SEQ ID NO: 5), API; 2 M NaOH; and sterile water for injection, USP. Disclosed below is at least one embodiment of the invention presented in a 0.1% CKPV dimer (SEQ ID NO: 5) batch of the composition weighing approximately 4 Kg. A contemplate range of percentages of individual components of the invention are disclosed for different size quantities of the invention.

One type of acrylic acid-based polymer is CARBOPOL®. CARBOPOL® is a registered trademark for high molecular weight, crosslinked, acrylic acid based polymers available from Noveon Pharmaceuticals. The amount of CARBOPOL® for use in the disclosed composition ranges from at least about 60 to 100 g or at least about 1.5-2.5% of the composition. A preferred amount of CARBOPOL® is at least about 80 g or at least about 2% of the composition. It will be apparent to those skilled in the art that other known gelling agents may be utilized in addition to or in place of CARBOPOL®, provided they are effective to form a gel.

Propylparaben, or 4-hydroxybenzoic acid propyl ester, is a well known preservative. See, The Merck Index p. 1350, 12$^{th}$ Ed. (Merck Research Laboratories, 1996). The amount of propylparaben for use in the disclosed composition ranges from at least about 1-3 g or 0.025-0.075% of the composition. A preferred amount of propylparaben is at least about 2 g or at least about 0.05% of the composition.

Methylparaben, or 4-hydroxybenzoic acid methyl ester, is a well known preservative. See, The Merck Index p. 1041, 12$^{th}$ Ed. (Merck Research Laboratories, 1996). The amount of methylparaben for use in the disclosed composition ranges from at least about 4-8 g or at least about 0.1-0.2% of the composition. A preferred amount of methylparaben is at least about 6 g or at least about 0.15% of the composition.

The preservatives may also be selected from the group consisting of phenoxyethanol, methylparaben, butylparaben, ethylparaben, propylparaben and potassium sorbate and combinations thereof.

Propylene glycol, or 1,2-propanediol, is a well known solvent with many uses in many areas of chemistry. See, The Merck Index p. 1348, 12$^{th}$ Ed. (Merck Research Laboratories, 1996). The amount of propylene glycol for use in the disclosed composition ranges from at least about 200-600 g or at least about 5-15% of the composition. A preferred amount of propylene glycol is at least about 400 g or at least about 10% of the composition.

The solvent may also be selected from the group consisting of ethanol, phenol, acetone, glycerol and isopropanol and combinations thereof.

EDTA, or N,N'-1,2-ethanediylbis[N-(carboxymethyl) glycine], is a well known chelating agent. See, The Merck Index p. 593, 12$^{th}$ Ed. (Merck Research Laboratories, 1996). The amount of EDTA for use in the disclosed composition ranges from at least about 2-6 g or at least about 0.05-0.15% of the composition. A preferred amount of EDTA is at least about 4 g or at least about 0.1% of the composition.

The chelating agent may also be selected from the group consisting of Coenzyme Q10, Zinc, L-Cysteine, L-Methionine, L-Lysine, Glutathione and EDTA and combinations thereof.

The CKPV (SEQ ID NO: 5) dimer is one form of dimer that may be used with the present invention. The amount of CKPV (SEQ ID NO: 5) for use in the disclosed composition ranges from at least about 2-6 g or 0.05-0.15% of the composition. A preferred amount of CKPV dimer (SEQ ID NO: 5) is at least about 4 g or 0.1% of the composition.

2M NaOH solution is a well known caustic used as an alkalizer. See, The Merck Index, p. 1477-8, 12$^{th}$ Ed. (Merck Research Laboratories, 1996). The amount of 2 M NaOH for use in the disclosed composition is that quantity sufficient to bring the composition to a preferred pH of 4.0±0.1.

The alkalizer may also be selected from the group consisting of N-(2-Hydroxyethyl)piperazine-N'-(2-ethanesulfonic acid) (hereon HEPES), 2M NaOH, 2-(N -Morpholino) ethanesulfonic acid (hereon MES hydrate), 3-(N -Morpholino)propanesulfonic acid (hereon MOPS), N-tris[Hydroxymethyl]methyl-3-aminopropanesulfonic acid (hereon TAPS), bis(2-Hydroxyethyl)amino -tris(hydroxymethyl) methane, (hereon Bis-Tris) or combinations thereof.

Sterile water for injection is a commonly known and used gelatinizing agent when taking powders or other solids to gels. Sterile water for injection for use in the disclosed composition is that quantity sufficient and up to at least about 3500-3550 g or at least about 87-89% of the composition.

Other gelatinizing agents may also be selected from the group consisting of water, sterile water, distilled water, sterile saline and combinations thereof.

A 4 Kg. 0.1 percent CKPV (SEQ ID NO: 5) dimer gel batch of the composition preferably comprises:

| | |
|---|---|
| Carbopol ® NF | 80.0 g |
| Propylparaben, NF | 2.0 g |
| Methylparaben, NF | 6.0 g |
| Propylene glycol, USP | 400.0 g |
| EDTA, USP | 4.0 g |
| The CKPV (SEQ ID NO:5) dimer, API | 4.0 g |
| 2M NaOH Solution | Quantity sufficient to pH 4.0 ± 0.1 |
| Sterile water for injection, USP | 3504 g |

As disclosed above and below, an effective amount of the CKPV (SEQ ID NO: 5) dimer, when used as a therapeutic, ranges in picomolar to nanomolar concentrations. Micromolar concentrations are more potently effective. The dosage of the pharmaceutical composition disclosed herein ranges from 50-150 µg/ml. A preferred dose of the pharmaceutical composition described herein is 100 µg/ml.

The following examples demonstrate the ability and application of alpha-MSH peptides to combat infection. Methods in microbiology, molecular biology, and cell culture used but not explicitly described in this disclosure have already been amply reported in the scientific literature. These methods are well within the ability of one skilled in the art.

Figure 16:
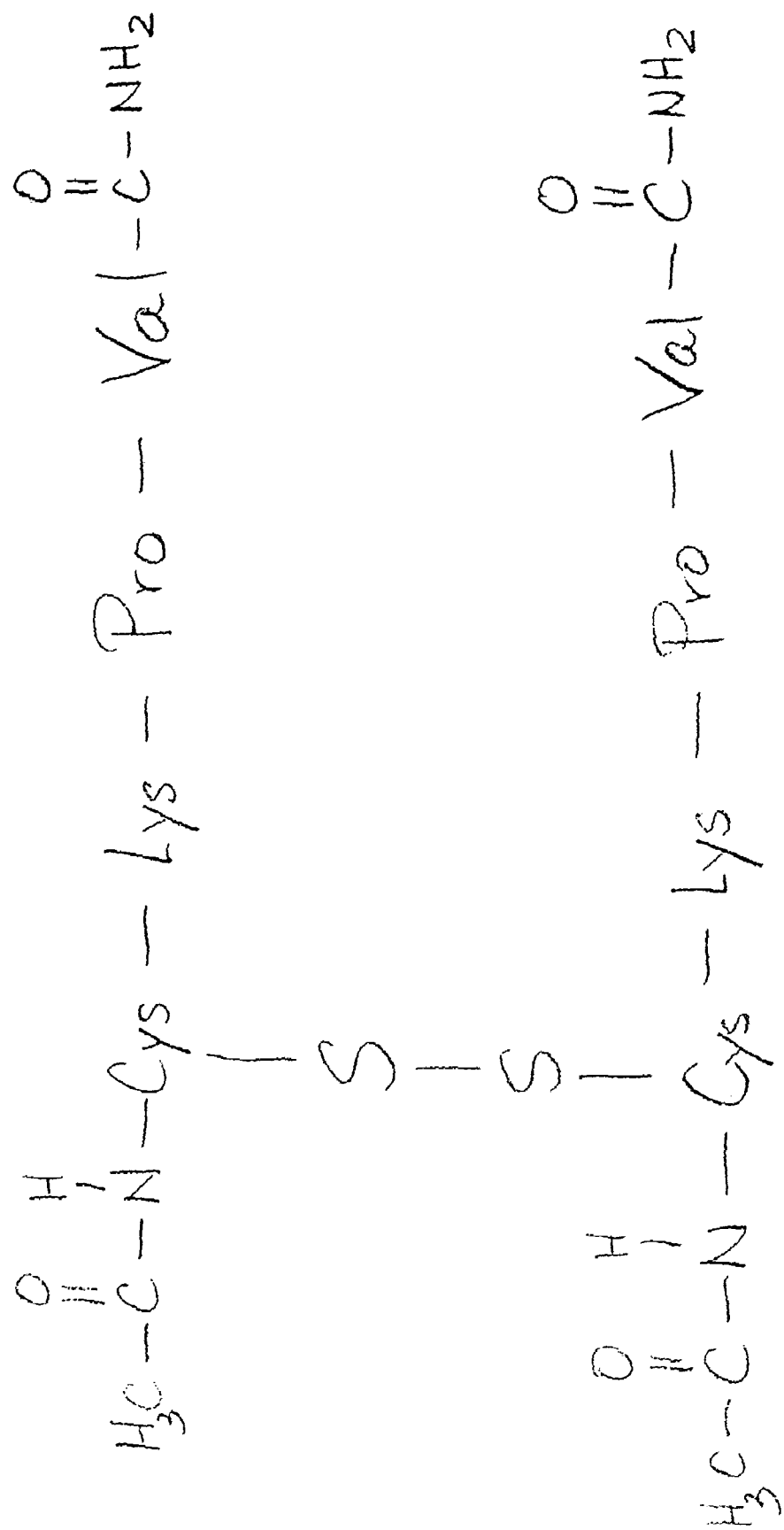
FIG. 16 shows a representation of one chemical structure of a KPV dimer.

The peptides used in the following examples include: a dimer of CKPV (SEQ ID NO: 5), alpha-MSH (1-13) (SEQ ID NO: 4), (4-10) (SEQ ID No: 2), (6-13) (SEQ ID NO: 3), and (11-13) (SEQ ID NO: 1), all of which were N-acetylated and C-amidated, and ACTH (1-39) (SEQ ID NO: 9) and (18-39) (SEQ ID NO: 10) (CLIP). These peptides were prepared by solid-phase peptide synthesis and purified by reversed phased high performance liquid chromatography. FIG. 16 shows a representation of one chemical structure for a KPV dimer. i.e., the CKPV dimer (SEQ ID NO: 5). Dimers can be formed by adding cysteines at the N-termini of any of the above polypeptides and allowing the cysteines of two polypeptides to form a disulfide bond. Both homo-dimers and hetero-dimers can be formed using this method.

A KPV dimer may be formed when the N-termini of two KPV peptides are joined by a linker. VPKC (SEQ ID NO: 5) -s-s CKPV (SEQ ID NO: 5) is an example of a KPV dimer formed by adding a cysteine at the N-terminal of a KPV peptide and allowing the cysteines of, then, two CKPV peptides to form a disulfide bond (-s-s-). In other words. VPKC (SEQ ID NO: 5) -s-s CKPV (SEQ ID NO: 5) is formed when two KPV (SEQ ID NO: 1) peptides are linked by a Cys-s-s-Cys-linker. The linker can be any kind of chemical bond that links the N-terminals of two KPV peptides together. It is preferred that the linker be -Cys-s-s-Cys-, -DCys-s-s-Cys-, -Pen-s-s-Cys-, -Pen-s-s-DCys-, -DPen-s-s-Cys-, -DPen-s-s-DCys-, -DPen-s-s-DPen-, -Pen-s-s-Pen-, -hCys-s-s-Cys-, -hCys-s-s-DCys-, -hCys-s-s-hCys-, -DhCys-s-s-DhCys-, -DhCys-s-s-hCys-, -hCys-s-s-Pen-, -hCys-s-s-DPen-, or -DhCys-s-s-DPen-.

It is more preferred that the linker be Cys-Cys-. The term "Pen" refers to Penicillamine. The Term "Cys" refers to Cysteine. The Term "hCy" refers to homocysteine. The prefix "D" refers to the dextro-form of an amino acid. Accordinaly, it is preferred that the KPV dimer be VPK-Cvs (SEQ ID NO: 5) -s-s-Cys-KPV (SEQ ID NO: 5), VPK-DCys (SEQ ID NO: 6)-s-s-Cys-KPV (SEQ ID NO: 5), VPK-Pen-s-s-Cys-KPV (SEQ ID NO: 5), VPK-Pen-s-s-DCys-KPV (SEQ ID NO: 6), VPK-DPen-s-s-Cys-KPV (SEQ ID NO: 5), VPK-DPen-s-s-DCys-KPV (SEQ ID NO: 6), VPK-DPen-s-s-DPen-KPV, VPK-Pen-s-s-Pen-KPV, VPK-hCys (SEQ ID NO: 7)-s-s-Cys-KPV (SEQ ID NO: 5), VPK-hCys (SEQ ID NO: 7)-s-s-DCys-KPV (SEQ ID NO: 6), VPK-hCys (SEQ ID NO: 7)-s-s-hCys-KPV (SEQ ID NO: 7), VPK-DhCys (SEQ ID NO: 8)-s-s-DhCys-KPV (SEQ ID NO: 8), VPK-DhCys (SEQ ID NO: 8)-s-s-hCys-KPV (SEQ ID NO: 7), VPK-hCys (SEQ ID NO: 7)-s-s-Pen-KPV, VPK-hCys (SEQ ID NO: 7)-s-s-DPen-KPV, or VPK-DhCys (SEQ ID NO: 8)-s-s-DPen-KPV. It is more preferred that the KPV dimer a CKPV (SEQ ID NO: 5) dimer, i.e., VPK-Cys (SEQ ID NO: 5)-s-s-Cys-KPV (SEQ ID NO: 5).

```
VPK-Cys              (SEQ ID NO: 8)

-s-s-Cys-KPV.        (SEQ ID NO: 8)
```

Although the specific amino acid sequences described here are effective, it is clear to those familiar with the art that amino acids can be substituted in the amino acid sequence or deleted without altering the effectiveness of the peptides. Thus, different KPV dimers are contemplated in this disclosure. Further, it is known that stabilization of the α-MSH sequence can greatly increase the activity of the peptide and that substitution of D-amino acid forms for L-forms can improve or decrease the effectiveness of peptides. For example, a stable analog of α-MSH, [Nle$^4$, D-Phe$^7$ α-MSH, which is known to have marked biological activity on melanocytes and melanoma cells, is approximately ten times more potent than the parent peptide in reducing fever. Holdeman, M. and Lipton, J. M., *Antipyretic Activity of a Potent α-MSH Analog, Peptides* 6, 273-5 (1985). Further, adding amino acids to the C-terminal α-MSH (11-13) sequence can reduce or enhance antipyretic potency (Deeter, L. B.; Martin, L. W.; Lipton, J. M., *Antipyretic Properties of Centrally Administered α-MSH Fragments in the Rabbit,* Peptides 9, 1285-8 (1989). Addition of glycine to form the 10-13 sequence slightly decreased potency; the 9-13 sequence was almost devoid of activity, whereas the potency of the 8-13 sequence was greater than that of the 11-13 sequence. It is known that Ac-[D-K$^{11}$] α-MSH 11-13-NH$_2$ has the same general potency as the L-form of the tripeptide α-MSH 11-13. Hiltz, M. E.; Catania, A.; Lipton, J. M., *Anti-inflammatory Activity of α-MSH (11-13) Analogs: Influences of Alterations in Stereochemistry,* Peptides 12, 767-71 (1991).

Substitution with the D-form of valine in position 13 or with the D-form of lysine at position 11 plus the D-form of valine at position 13 resulted in greater anti-inflammatory activity than with the L-form tripeptide. Thus, a dimer created with the D-form may be another effective KPV dimer. These examples indicate that alterations in the amino acid characteristics of the peptides can influence activity of the peptides or have little effect, depending upon the nature of the manipulation. It is also believed that biological functional equivalents may be obtained by substitution of amino acids having similar hydropathic values. Thus, for example, isoleucine and leucine, which have a hydropathic index +4.5 and +3.8, respectively, can be substituted for valine, which has a hydropathic index of +4.2, and still obtain a protein having like biological activity. Alternatively, at the other end of the scale, lysine (−3.9) can be substituted for arginine (−4.5), and so on. In general, it is believed that amino acids can be successfully substituted where such amino acid has a hydropathic score of within about +/−1 hydropathic index unit of the replaced amino acid. The antimicrobial properties of biological functional equivalents can be measured through their inhibitory effect on the colony forming units in bacteria or fungi, or through their inhibitory effect on the HIV expression or transcription, as disclosed in the examples of the description of this invention.

Statistical significance disclosed in the examples below was analyzed using one-way analysis of variance and the Student's t test. Probability values greater than 0.05 were considered significant.

EXAMPLE I

This example illustrates the anti-microbial properties of alpha-MSH peptides against *Staphylococcus aureus*.

Cultures of *S. aureus* (ATCC 29213) were obtained from the collection of the Department of Microbiology, Ospedale Maggiore di Milano. *S. aureus* ($1 \times 10^6$/ml in Hank's balanced salt solution) was incubated in the presence or absence of alpha-MSH (1-13) (SEQ ID NO: 4), alpha-MSH (11-13) (SEQ ID NO: 1), or the CKPV (SEQ ID NO: 5) dimer at concentrations in the range of $10^{-15}$ to $10^{-4}$ M for two hours at 37° C. Cells were then washed in cold distilled water and diluted with HBSS to a concentration of 100 organisms/ml. One-milliliter aliquots were dispensed on blood agar plates and incubated for 24 hours at 37° C. Viability of the microorganisms was estimated from the colonies formed. In another set of experiments, 500 units of urokinase, a *S. aureus* growth enhancer, were also incubated with the bacteria ($10^5$/100 ml ) for four hours at 37° C. in a shaking water bath together with the peptides.

Figure 2:
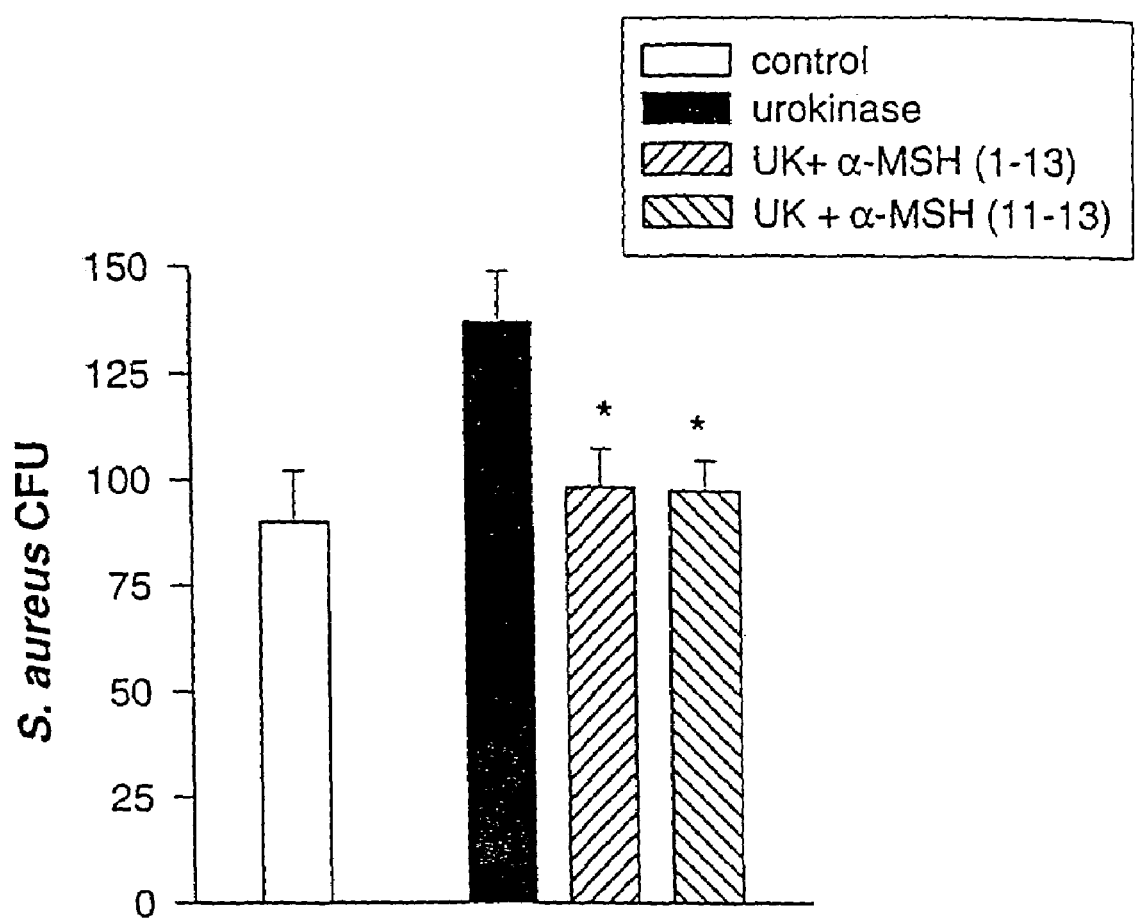
FIG. 2 shows the effects of alpha-MSH peptides on urokinase induced growth of *S. aureus*.

FIG. 1 shows that alpha-MSH (1-13) (SEQ ID NO: 4), alpha-MSH (11-13) (SEQ ID NO: 1), and the CKPV (SEQ ID NO: 5) dimer all inhibited *S. aureus* colony formation. These inhibitory effects occurred over a wide range of concentrations and were significant (p>0.01) with peptide concentrations of $10^{-12}$ to $10^{-4}$ M. FIG. 2 shows that alpha-MSH (1-13) (SEQ ID NO: 4) and alpha-MSH (11-13) (SEQ ID NO: 1) at concentrations of $10^{-6}$ M significantly countered the growth enhancing effect of urokinase. Thus, alpha-MSH peptides can inhibit the growth of *Staphylococcus aureus*, an agent known to cause toxic shock syndrome associated with tampon use, vaginitis, UTIs, urethritis, and balanoposthitis.

EXAMPLE II

This example illustrates the anti-fungal properties of alpha-MSH peptides against *Candida albicans*.

Clinical isolates of *C. albicans* were obtained from the collection of the Department of Microbiology, Ospedale Maggiore di Milano. Cultures of *C. albicans* were maintained on Sabouraud's agar slants and periodically transferred to Sabouraud's agar plates and incubated for 48 hours at 28° C. To prepare stationary growth-phase yeast, a colony was taken from the agar plate, transferred into 30 ml of Sabouraud-dextrose broth, and incubated for 72 hours at 32° C. Cells were centrifuged at 1000× g for ten minutes, and the pellet was washed twice with distilled water. Cells were counted and suspended in Hank's balanced salt solution ("HBSS") to the desired concentration. Viability, determined by exclusion of 0.01% methylene blue, remained greater than 98%.

At $1\times10^6$/ml in HBSS, these fungi were incubated in the presence or absence of alpha-MSH (1-13) (SEQ ID NO: 4), alpha-MSH (11-13) (SEQ ID NO: 1), or the CKPV (SEQ ID NO: 5) dimer at concentrations ranging from $10^{-15}$ to $10^{-4}$ M for two hours at 37° C. Cells were then washed in cold distilled water and diluted with HBSS to a concentration of 100 organisms/ml. One-milliliter aliquots were then dispensed on blood agar plates and incubated for 48 hours at 37° C. The organism's viability was estimated from the number of colonies formed.

Figure 3:
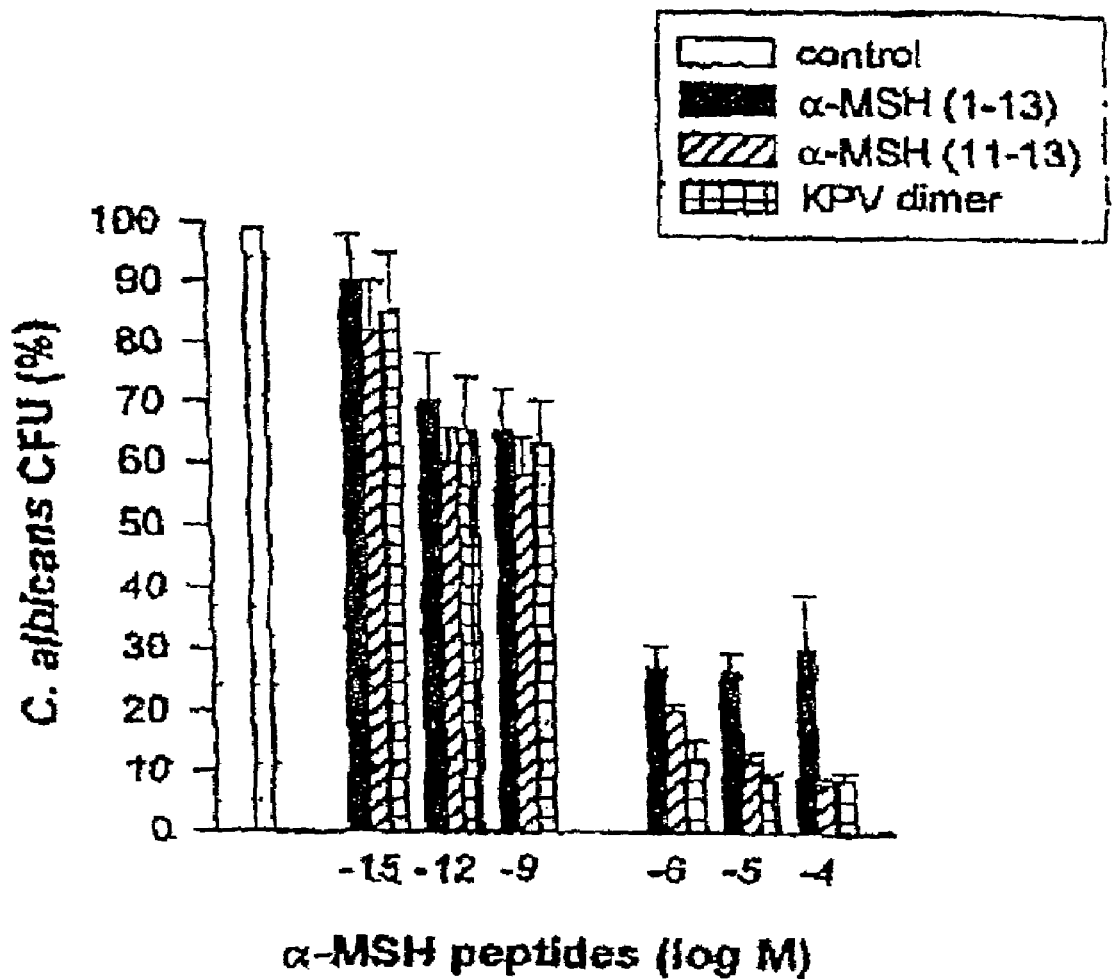
FIG. 3 shows the inhibitory effects of alpha-MSH peptides on the growth of *C. albicans*.

FIG. 3 shows that alpha-MSH(1-13) (SEQ ID NO: 4), alpha-MSH(11-13) (SEQ ID NO: 1), and the CKPV (SEQ ID NO: 5) dimer greatly reduced the ability of *C albicans* to form colonies at concentrations ranging from $10^{-12}$ to $10^{-4}$ M ($p<0.01$ vs. control). Thus, this demonstrates that alpha-MSH peptides can inhibit the growth of *Candida albicans*, an agent known to cause candidiasis, vaginitis, urethritis, and balanoposthitis.

EXAMPLE III

This example compares the anti-infection activities of alpha-MSH peptides to fluconazole, an established anti-fungal agent.

Figure 4:
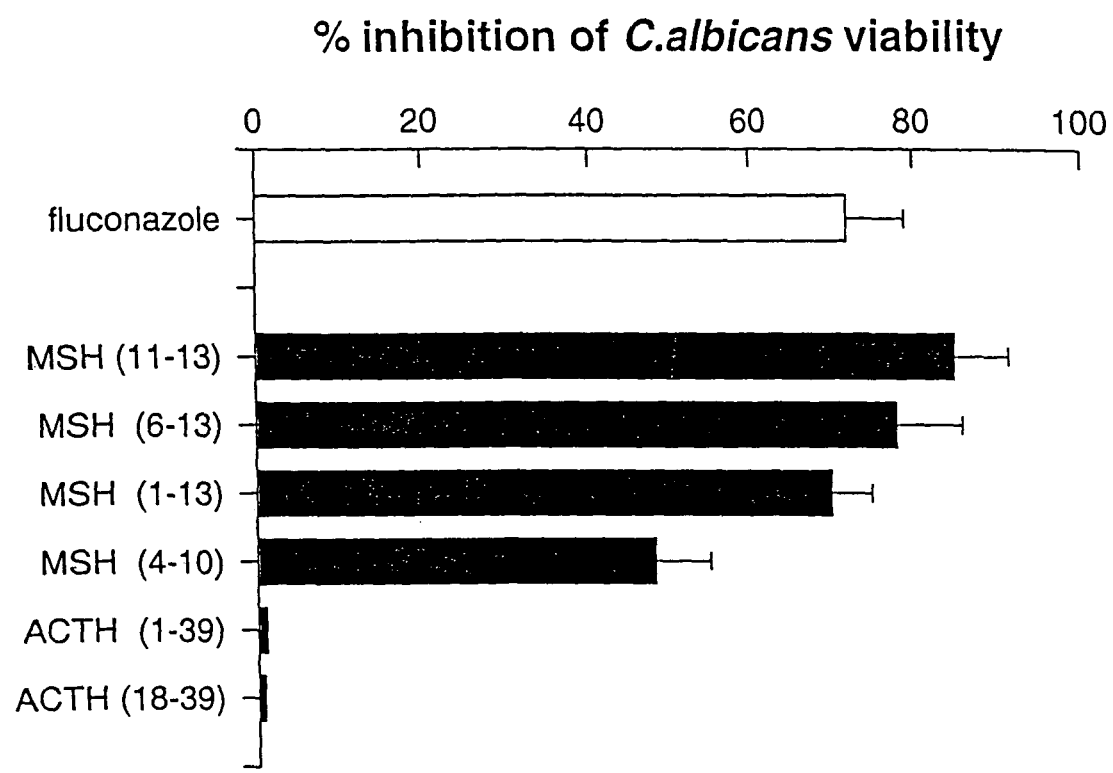
FIG. 4 compares the anti-fungal activities of alpha-MSH peptides with fluconazole.
Figure 5:
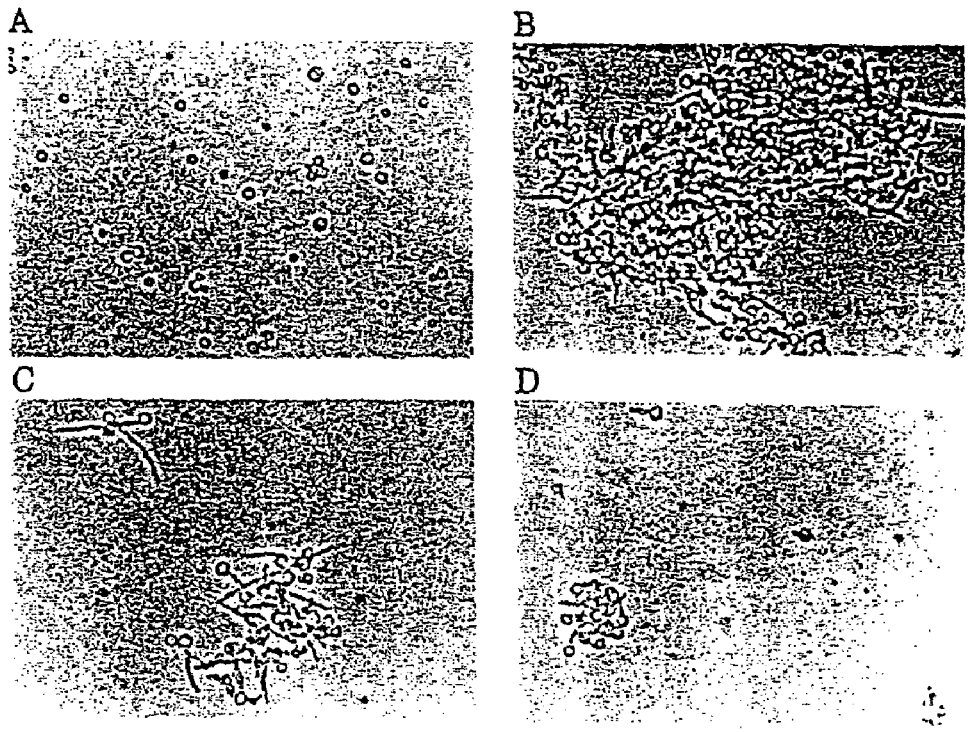
FIGS. 5A to 5D show the inhibitory effects of alpha-MSH peptides on *C. albicans*' germ tube formation.

Alpha-MSH (1-13) (SEQ ID NO: 4), (4-10) (SEQ ID NO: 2), (6-13) (SEQ ID NO: 3), (11-13) (SEQ ID NO: 1), ACTH (1-39) (SEQ ID NO: 9), (18-39) (SEQ ID NO: 10), and fluconazole, at concentrations of $10^{-6}$ to $10^{-4}$ M, were tested against *C. albicans* using the same procedures as in Example II. FIG. 4 shows that compared with fluconazole, alpha-MSH (11-13) (SEQ ID NO: 1), (6-13) (SEQ ID NO: 3), and (1-13) (SEQ ID NO: 4) were most effective against *C. albicans*. Their inhibitory activities were similar to fluconazole at the same molar concentration. In contrast, the "core" alpha-MSH sequence (4-10) (SEQ ID NO: 2), which has behavioral effects but little anti-inflammatory activity, caused approximately 50% inhibition of colony forming units (CFU). Although this inhibitory effect was substantial ($p<0.01$ vs. control), it was significantly less potent that alpha-MSH fragments bearing the KPV signal sequence, i.e. alpha-MSH (6-13) (SEQ ID NO: 3) and (11-13) (SEQ ID NO: 1) ($p<0.01$), or the parent molecule alpha-MSH (1-13) (SEQ ID NO: 4) ($p<0.05$). FIG. 4 also shows that ACTH (1-39) (SEQ ID NO: 9) and the ACTH fragment (18-39) (SEQ ID NO: 10) did not reduce *C. albicans* viability. Even at a higher concentration of $10^{-4}$ M, which is not shown in the figures, ACTH peptides were likewise ineffective.

Thus, this example demonstrates that alpha-MSH peptides are as effective as fluconazole in inhibiting *Candida's* growth.

EXAMPLE IV

This example illustrates that alpha-MSH peptides inhibit the germination or germ tube formation of *C. albicans*. Germ tube formation is a significant part of the pathogenesis of *C. albicans* infection. This pathogenesis involves adhesion to host epithelial and endothelial cells and morphologic switching from the ellipsoid blastospore to various filamentous forms, e.g. germ tubes, pseudohyphae, and hyphae. Gow, N. A., *Germ Tube Growth of Candida albicans, Curr. Topics Med. Myco.* 8, 43-55 (1997).

*C. albicans* from stationary phase cultures were washed twice with distilled water and suspended in HBSS to a final concentration of $2\times10^6$/ml. Hyphal growth was induced by addition of 10% inactivated horse serum (GIBCO/BRL, Paisley, Great Britain) to yeast incubated for 45 minutes at 37° C. with continuous shaking. Horse serum was then removed by washing cells twice with HBSS, and incubation was further continued for 60 minutes at 37° C. in the presence of alpha-MSH (1-13) (SEQ ID NO: 4), (6-13) (SEQ ID NO: 3), or (11-13) (SEQ ID NO: 1) at a concentration of $10^{-6}$ M with continuous shaking. The percentage of filamentous cells was evaluated under a light microscope with the aid of a hemocytometer. Experiments were run in triplicate and at least 200 cells were scored. Photomicrographs were taken with a MC100 camera attached to an Axioskop Zeiss microscope.

FIGS. 5A to 5D show that co-incubation of *C. albicans* with alpha-MSH (1-13) (SEQ ID NO: 4) or (11-13) (SEQ ID NO: 1) inhibited germ tube formation induced by horse serum. Alpha-MSH (1-13) (SEQ ID NO: 4) caused 28-32% reduction in the number of filamentous cells while alpha-MSH (11-13) (SEQ ID NO: 1) caused 54-58% reduction. Although not shown in the figures, alpha-MSH (6-13) (SEQ ID NO: 3) similarly had approximately 50% reduction in the number of filamentous cells. Thus, this demonstrates alpha-MSH peptides can inhibit one mode of *Candida* pathogenesis by inhibiting its germ tube formation.

EXAMPLE V

Reduced killing of pathogens is a dire consequence of therapy with corticosteroids and other nonsteroidal anti-inflammatory drugs during infection. Stevens, D. L., *Could Nonsteroidal Anti-inflammatory Drugs (NSAIDs) Enhance Progression of Bacterial Infections to Toxic Shock Syndrome?, Clin. Infect. Dis.* 21, 977-80 (1997); Capsoni, F., et. al., *Effect of Corticosteroids on Neutrophil Function: Inhibition of Antibody-dependent Cell-Mediated Cytotoxicity (ADCC), J. Immunopharmacol.* 5, 217-30 (1983). This example illustrates that alpha-MSH peptides inhibit the growth of infectious agents without comprising the ability of human neutrophils to combat these infections. This example further shows that alpha-MSH peptides can actually enhance the ability of neutrophils to kill these infectious agents.

Venous blood (20 ml) from healthy volunteers was anticoagulated with heparin. Neutrophils were then isolated using dextran sedimentation and centrifugation with Ficoll-Hypaque (Sigma Chemical Co., St. Louis, Mo., USA). Erythrocytes were lysed via hypotonic shock with the resulting neutrophils representing at least 97% of the cell suspension. Cell viability, estimated by trypan blue exclusion, was greater than 98%. Neutrophils were resuspended in HBSS for the experiments.

*C. albicans* ($1\times10^6$) were opsonized with human AB serum in a shaking water bath for 30 minutes at 37° C. They were then incubated with neutrophils in the presence of medium alone, or medium with alpha-MSH (1-13) (SEQ ID NO: 4) or alpha-MSH (11-13) (SEQ ID NO: 1) in concentrations ranging from $10^{-15}$ to $10^{-4}$ M in a shaking water bath for two hours at 37° C. After incubation, the culture tubes were placed on ice to stop growth, and extracellular organisms were washed twice with centrifugation at 1000-× g at 4° C. A 2.5% sodium deoxycholate solution was added to the suspension, and the tubes were shaken for five minutes. Cold distilled water was then added to obtain a suspension of $10^6$ cells/ml. Two 1/100 serial dilutions in HBSS were made to obtain a final suspension of 100 cells/ml. One-milliliter aliquots were then dispensed on blood agar plates and incubated for 48 hours at 37° C. Colony forming units were counted at the end of the incubation period with experiments running in triplicate and repeated using blood from five different donors.

Figure 6:
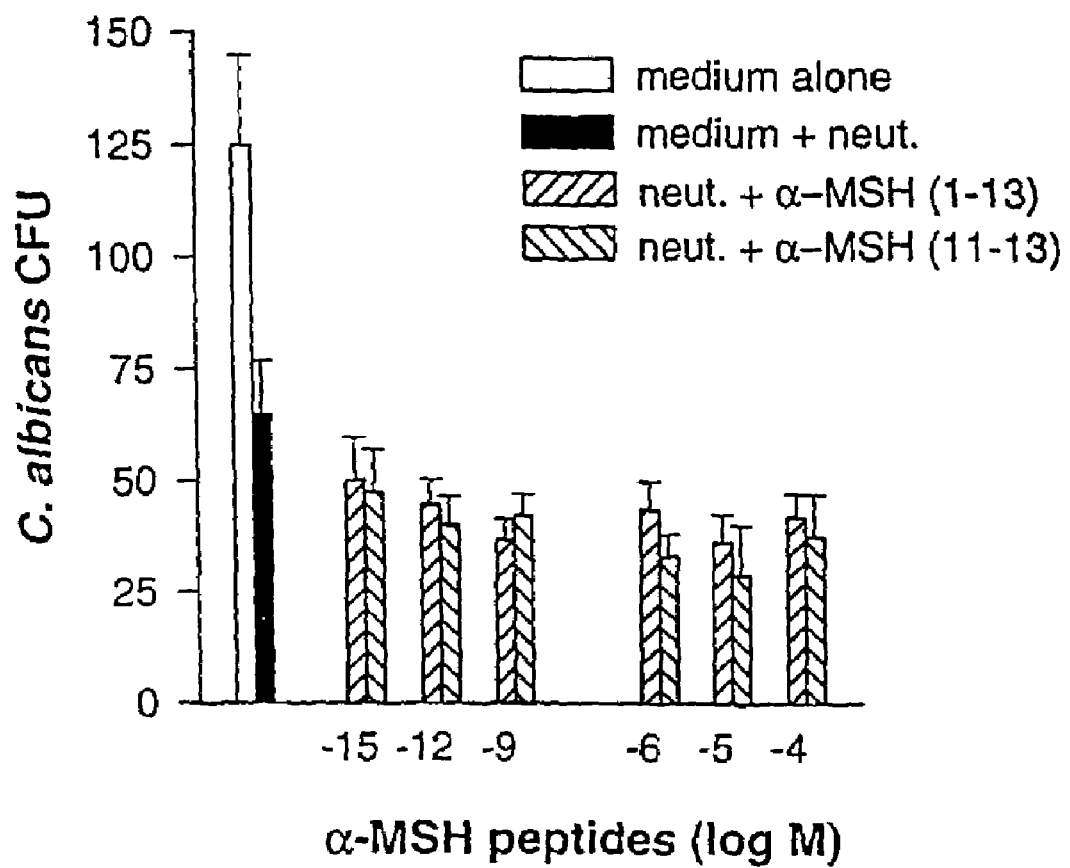
FIG. 6 shows the enhanced neutrophil-killing effects of alpha-MSH peptides against *C. albicans*.

FIG. 6 shows that alpha-MSH (1-13) (SEQ ID NO: 4) and (11-13) (SEQ ID NO: 1) actually enhanced neutrophil killing of *C. albicans* when administered at concentrations ranging from $10^{-12}$ to $10^{-4}$ M ($p<0.01$). This shows that this enhanced killing occurred over a very broad range of concentrations including picomolar concentration, which is similar to the concentration of alpha-MSH found in human plasma.

Thus, this example demonstrates that alpha-MSH peptides can simultaneously combat against infection and inflammation, which may also be applied to candidiasis, vaginitis, urethritis, balanoposthitis, or hemorrhoids.

EXAMPLE VI

This example suggests the cellular mechanism by which alpha-MSH peptides exert anti-microbial properties in general, and anti-fungal properties in particular.

*C. albicans* ($10^6$/ml), permeabilized with toluene/ethanol, were incubated at 37° C. with continuous shaking in the presence or absence of $10^{-6}$ M alpha-MSH (1-13) (SEQ ID NO: 4), (11-13) (SEQ ID NO: 1), or forskolin, an agent known to increase intracellular cAMP. The reactions were stopped after three minutes by the addition of ice cold ethanol. cAMP levels were measured in duplicate using a commercial enzyme immunoassay kit (Amersham, United Kingdom) after extraction via the liquid-phase method according to the manufacturer's instructions. In a related experiment, *C. albicans* was also exposed to dideoxyadenosine (ddAdo, Sigma), a potent inhibitor of adenylyl cyclase, at concentrations of 25, 50, and $100\times10^{-5}$ M for two hours, and to alpha-MSH peptides for two additional hours. The effects of forskolin and ddAdo on the ability of *C. albicans* to form colonies were determined according to the procedures described in Example II.

Figure 7:
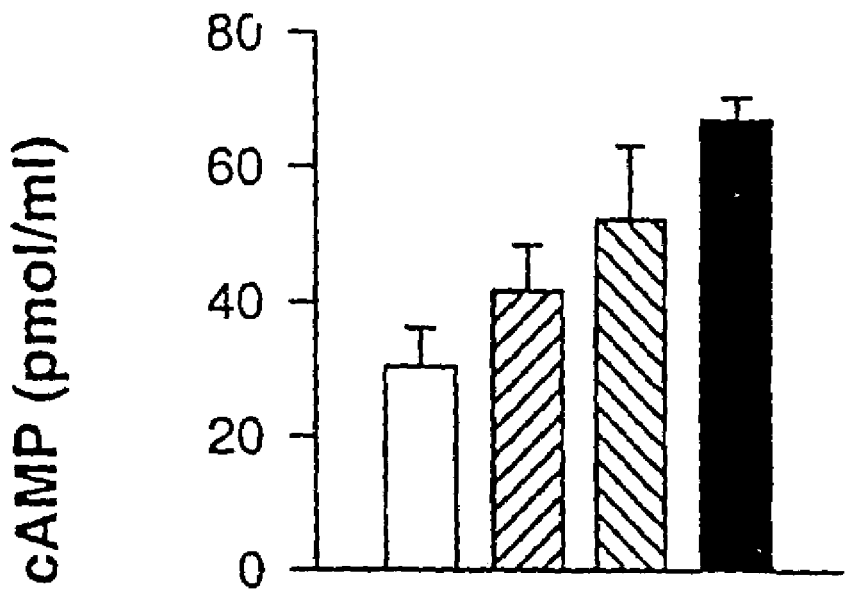
FIGS. 7, 8, and 9 show the mechanism by which alpha-MSH peptides inhibit the growth of *C. albicans*.
Figure 8:
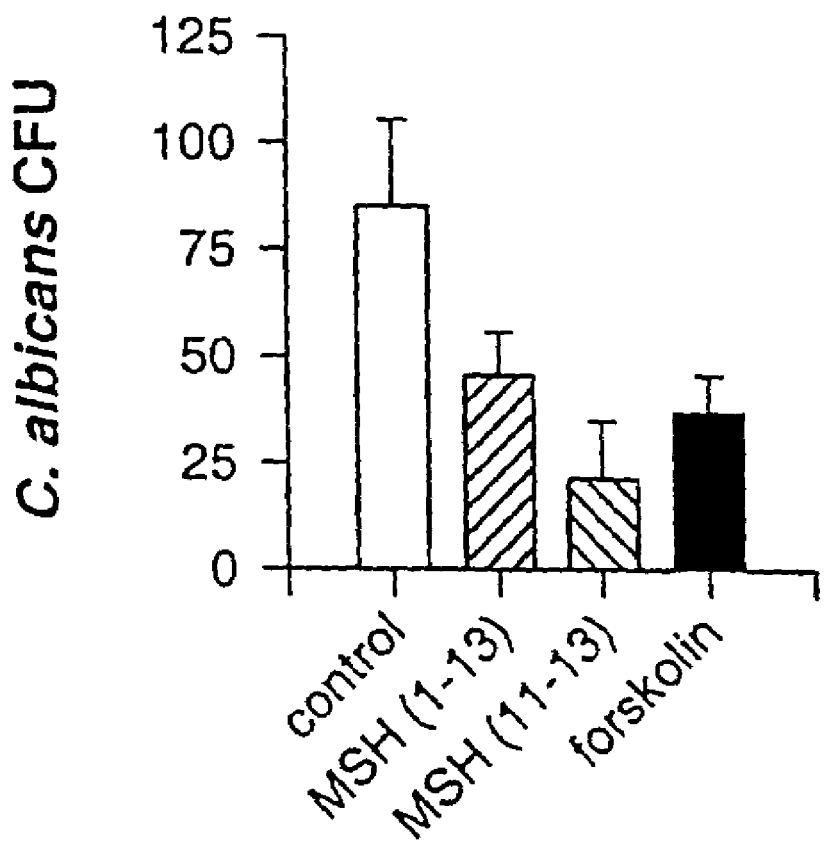
Figure 9:
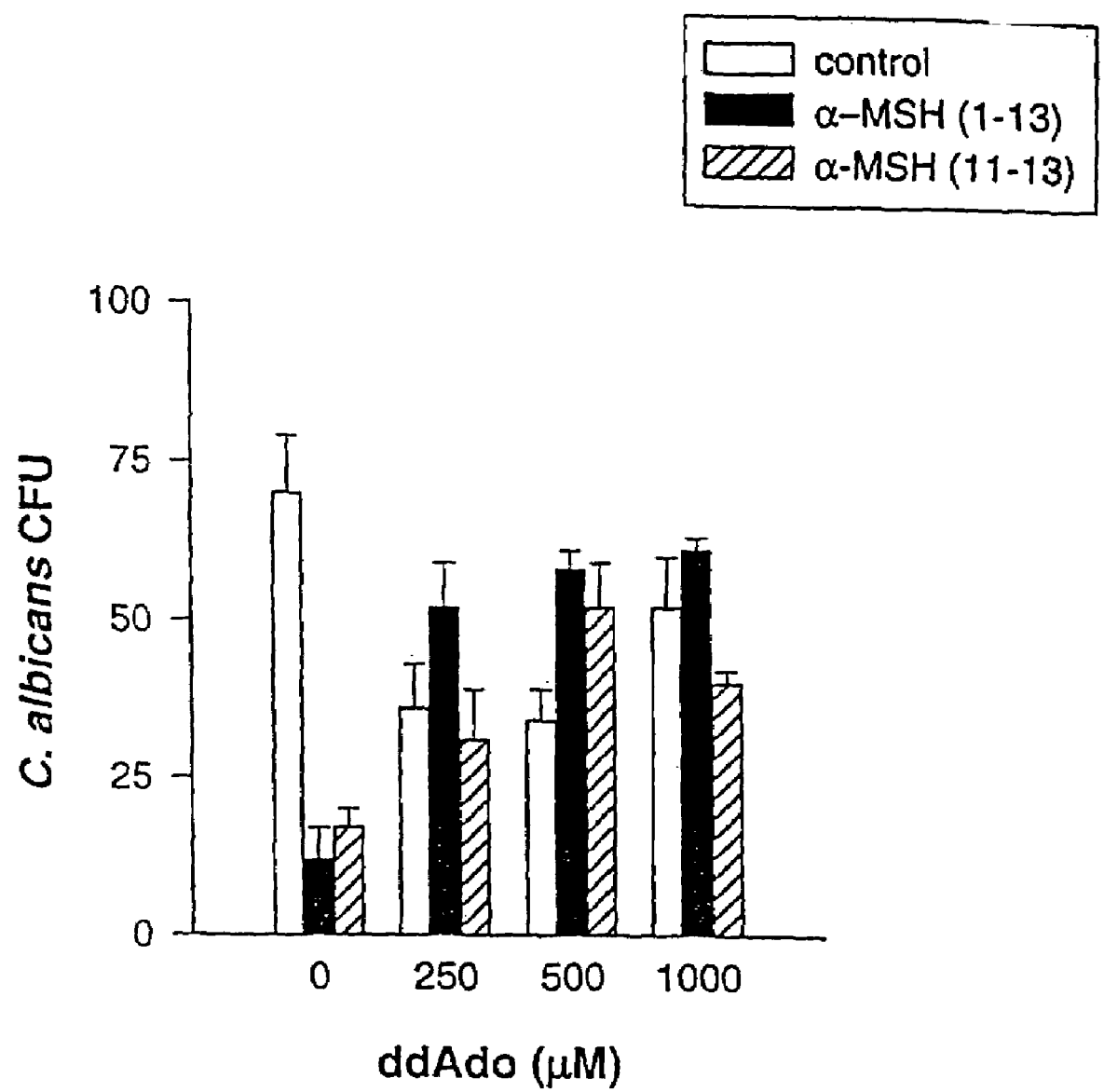

FIG. 7 shows that alpha-MSH (1-13) (SEQ ID NO: 4) and (11-13) (SEQ ID NO: 1) enhanced cAMP content in *C. albicans*. This cAMP increase was of the same order of magnitude as that induced by equimolar forskolin. FIG. 8 shows that along with alpha-MSH (1-13) (SEQ ID NO: 4) and (11-13) (SEQ ID NO: 1), forskolin also significantly inhibited the growth of *C. albicans* relative to the control group ($p<0.01$). FIG. 9 shows that ddAdo has the ability to reverse the effect of alpha-MSH (1-13) (SEQ ID NO: 4) and (11-13) (SEQ ID NO: 1) on the growth of *C. albicans*.

This example demonstrates that alpha-MSH peptides most likely inhibit growth of *C. albicans* and other microorganisms by increasing its cAMP level, which in turn inhibits mRNA and protein synthesis. See e.g., Bhattacharya A., et. al., *Effect of Cyclic AMP on RNA and Protein Synthesis in Candida albicans, Biochem, Biophysics. Res. Commun.*, 77:1433-44 (1977).

EXAMPLE VII

This example illustrates the ability of alpha-MSH peptides to inhibit viral replication in human cells. More specifically, alpha-MSH inhibited the replication and expression of HIV-1 in chronically infected human monocytes.

The chronically HIV-1 infected promonocytic U1 cell line is an in vitro model of latent HIV infection in monocytes. These cells carry two integrated proviral copies of HIV, and constitutive expression of HIV is very low. Viral replication, however, as measured by RNA transcription, p24 antigen, or reverse transcriptase release, can be activated with different stimuli such as TNF-α, IL-6, IL-10, PMA or crowding of cells.

To determine the effects of alpha-MSH peptides on HIV replication, these cells were maintained in log phase of growth in a complete culture medium (RPMI 1640 supplemented with 10 mM Hepes), 2 mM L-glutamine (Sigma-Aldrich), 10% heat-inactivated FCS (Hyclone Laboratories, Logan, Utah, USA), penicillin at 100 units/ml and streptomycin at 100 μg/ml (Gibco Laboratories, Grand Island, N.Y.) in log phase of growth. Pilot experiments were first performed to determine optimal cell density, stimuli concentration, and kinetics of HIV-1 p24 antigen production using these culture conditions. Before use, cells were washed three times with HBSS to remove extracellular viruses. Cells were then plated on 24-well flat-bottomed plates at a concentration of $2\times10^5$/ml (final volume of one ml) with medium alone or medium plus TNF-α (10 ng/ml) (R&D Systems, Oxford, England, UK) in the presence or absence of alpha-MSH (1-13) (SEQ ID NO: 4) or (11-13) (SEQ ID NO: 1) in concentrations from $10^{-15}$ to $10^{-4}$ M.

In further experiments, alpha-MSH (11-13) (SEQ ID NO: 1), alone at $10^{-5}$ M, was added to U1 cells stimulated with TNF-α (10 ng/ml), IL-6 (20 ng/ml), IL-10 (20 ng/ml) (R&D Systems, Oxford, England, UK), PMA (1 ng/ml) (Sigma-Aldrich), or in crowding conditions. Crowding was achieved by seeding U1 cells at a density of $2\times10^5$/ml and maintaining them in culture at 37° C. in 5% $CO_2$ without changing media for seven days. Cultures activated with cytokines or PMA were maintained for only 48 hours. Supernatants were then removed by centrifugation and assayed for p24 antigen using commercially available ELISA kits from Cellular Products, Inc. in Buffalo, N.Y., USA. Reverse transcriptase releases were also measured using a commercially available kit, ELISA Retrosys RT assay from Innovagen, Lund, Sweden. For these experiments, addition of alpha-MSH (11-13) (SEQ ID NO: 1) occurred on day one, and each condition was tested in triplicate.

Figure 10:
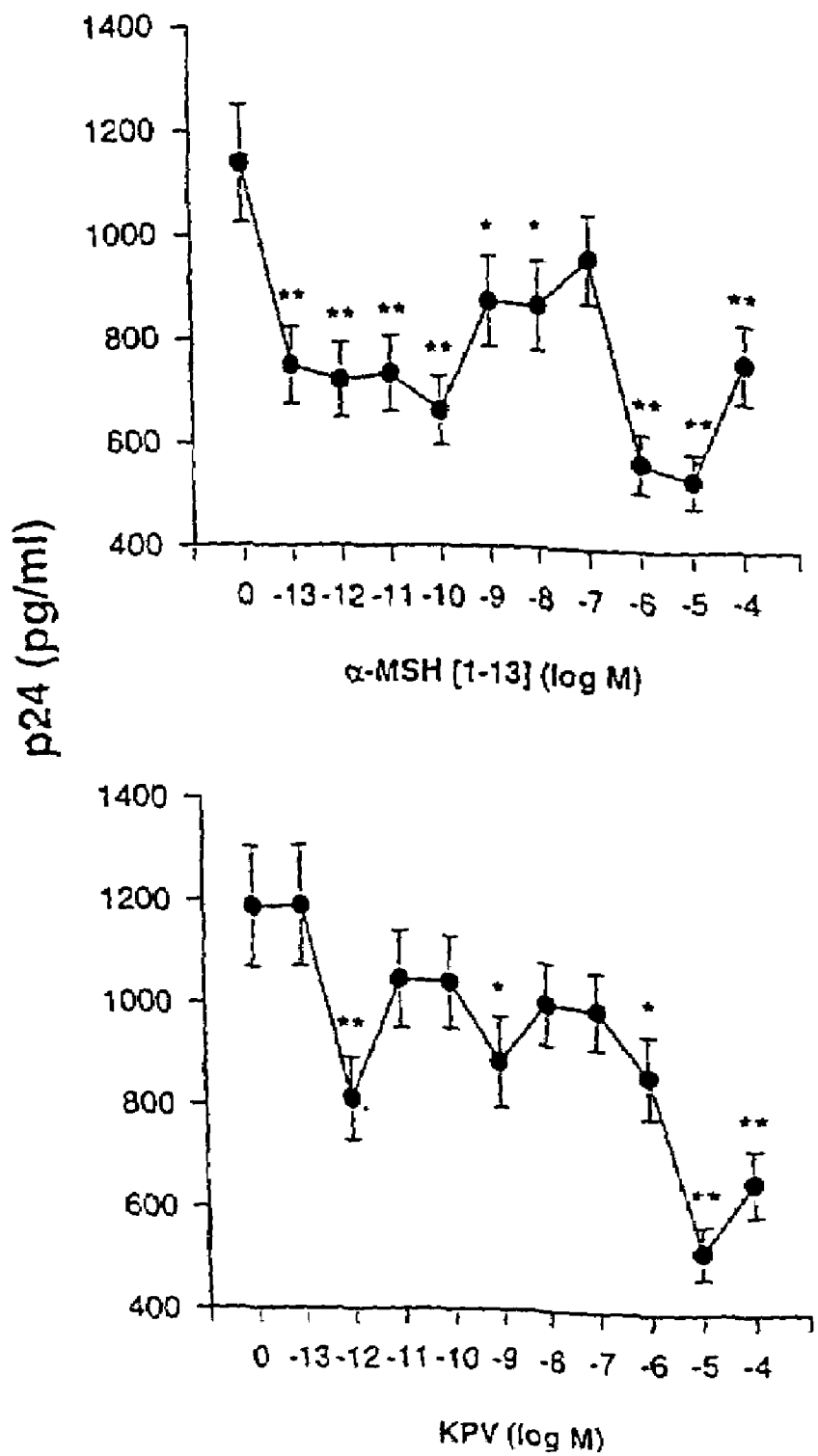
FIGS. 10-13 show the inhibitory effects of alpha-MSH peptides on viral replication and expression in chronically infected cells.
Figure 11:
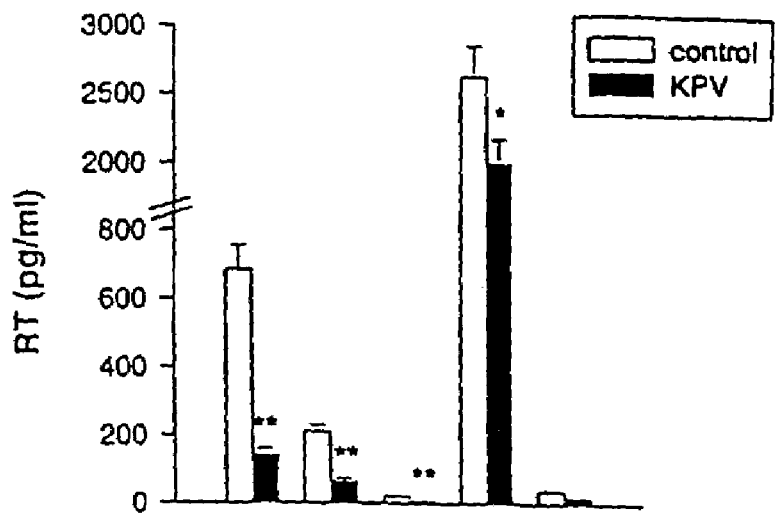
Figure 11:
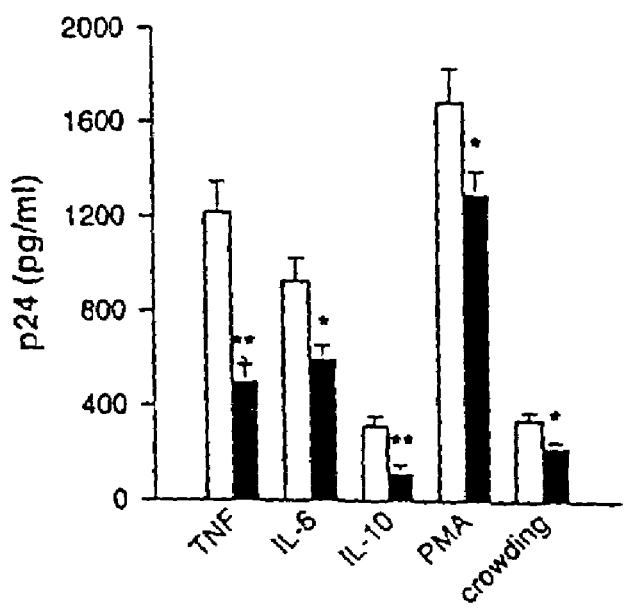
Figure 12:
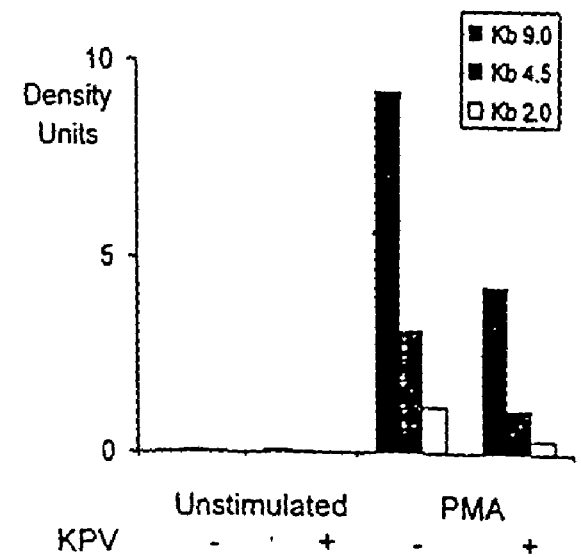
Figure 12:
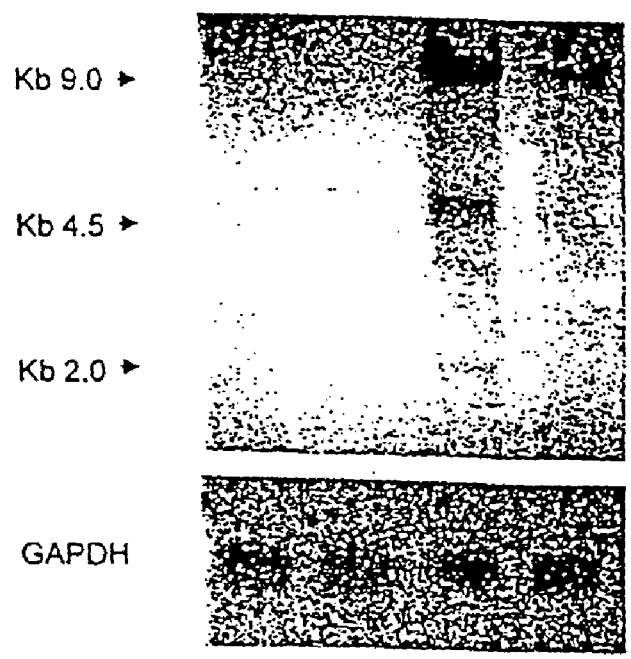

FIG. 10 shows that alpha-MSH (1-13) (SEQ ID NO: 4) and (11-13) (SEQ ID NO: 1) significantly inhibited p24 antigen release from TNF-α stimulated U1 cells over a broad range of concentrations. The most effective concentration for both peptides was $10^{-5}$ M, causing 52.7% and 56.0% inhibition respectively. FIG. 11 shows that alpha-MSH (11-13) (SEQ ID NO: 1) also inhibited p24 antigen and reverse transcriptase release from U1 cells induced by IL-6, IL-10, PMA and in crowding condition. In addition, FIG. 12 shows that alpha-MSH(11-13) (SEQ ID NO: 1) also inhibited the transcription of both spliced and unspliced HIV-1 RNA in PMA stimulated U1 cells as measured by Northern Blot analysis.

Thus, this example demonstrates that alpha-MSH peptides can inhibit transcription of viral genes through mediation of the TNF-α, IL-6 and IL-10 pathways.

EXAMPLE VIII

This example further illustrates the ability of alpha-MSH to inhibit viral replication and activation. More specifically, this example illustrates that the addition of a neutralizing antibody to alpha-MSH in U1 cells substantially increased p24-antigen release.

U1 cells were cultured similarly as described in Example VII. Endogenous alpha-MSH produced by U1 cells was blocked with an affinity purified rabbit-anti-alpha-MSH antibody (Euro-Diagnostica, Malmo, Sweden) diluted 1:250 with medium. The control antibody was a rabbit IgG at the same dilution. Cells ($2 \times 10^5$/ml) treated with the anti-alpha-MSH or the control antibody were coincubated with medium or PMA (1 ng/ml). After 48-hour incubation at 37° C., supernatants were separated and tested for p24 antigen release. In crowding experiments with U1 cells cultured as described above, the anti-alpha-MSH antibody or the control IgG was added on day one and the supernatants were harvested on day seven.

Figure 13:
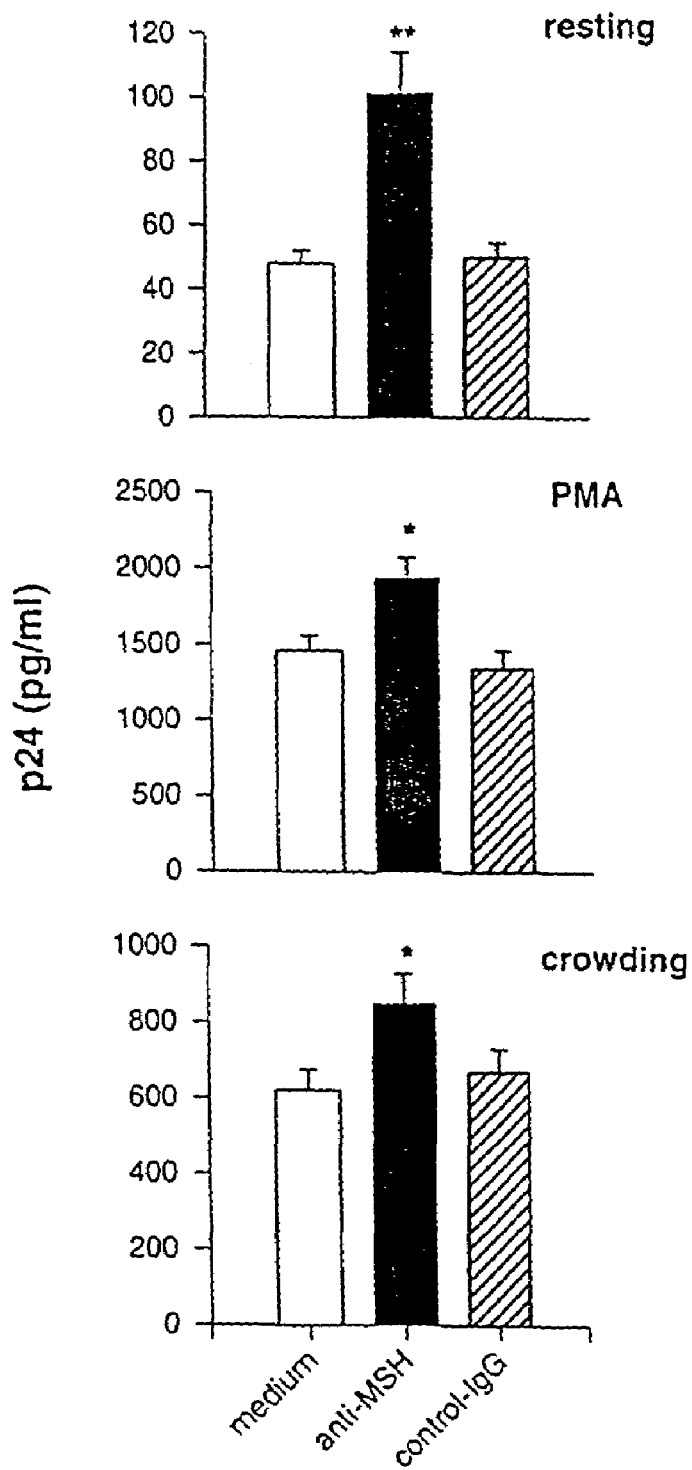

FIG. 13 shows that blocking alpha-MSH in resting, PMA induced, or crowded U1 cells significantly increased the release of p24 antigen. This example strongly implies that viral replication is affected by alpha-MSH.

EXAMPLE IX

This example illustrates the mechanism by which alpha-MSH peptides inhibit viral replication and expression. More specifically, alpha-MSH peptides inhibited TNF-α induced NF-κB activation and binding.

To determine the level of NF-κB activity, nuclear extracts were prepared from $20 \times 10^6$ U1 cells ($2 \times 10^5$/ml in complete medium) stimulated for four hours with TNF-α (20 ng/ml) in the presence or absence of $10^{-5}$ M alpha-MSH (11-13) (SEQ ID NO: 1). Cells were washed once with cold PBS, and twice with buffer A (10 mM Hepes pH 7.9, 1.5 mM $MgCl_2$, 10 mM KCl, 0.5 mM PMSF and 0.5 mM DTT), centrifuged, and incubated for ten minutes on ice in buffer A plus 0.1% NP-40. Afterwards, the supernatants were removed, and the nuclear pellets were resuspended in 15 µl of buffer C (20 mM Hepes pH 7.9, 1.5 mM $MgCl_2$, 0.42 M KCl, 0.2 mM EDTA, 25% glycerol, 0.5 mM PMSF, and 0.5 mM DTT), incubated for 15 minutes on ice, mixed, and then centrifuged. The supernatants were diluted with 75 µl of modified buffer D (20 mM Hepes, pH 7.9, 0.05 mM KCl, 0.2 mM EDTA, 20% glycerol, 0.5 mM PMSF, and 0.5 mM DTT) and stored at −80° C. The binding reaction was carried out for fifteen minutes at room temperature with 10 µg of nuclear extract protein and 0.5 ng of $^{32}$P-labeled NF-κB (30,000 cpm/µl) or AP1 consensus in buffer A (12 mM Tris-HCl pH 7.8, 60 mM KCl, 0.2 mM EDTA, 0.3 mM DTT), plus 10% glycerol, 2 µg/ml bovine serum albumin and 1 µg/ml single stranded DNA (Pharmacia Biotech). The oligonucleotides for NF-κB used in these studies were: + gat cca agg gga ctt tcc gct ggg gac ttt cca tg (SEQ ID NO: 11), and − gat cca tgg aaa gtc ccc agc gga aag tcc cct tg (SEQ ID NO: 12). Each oligonucleotide was annealed to its complementary strand and end-labeled with $^{32}$P-γ-ATP using polynucleotide kinase. For the determination of specific bands, nuclear extracts were first incubated with 100 fold excess unlabeled probe for five minutes, before incubation with a labeled probe. The mixtures were then run on 5% (30:1) acrylamide gel in 1×TBE. The gels were dried and autoradiographed.

Figure 14:
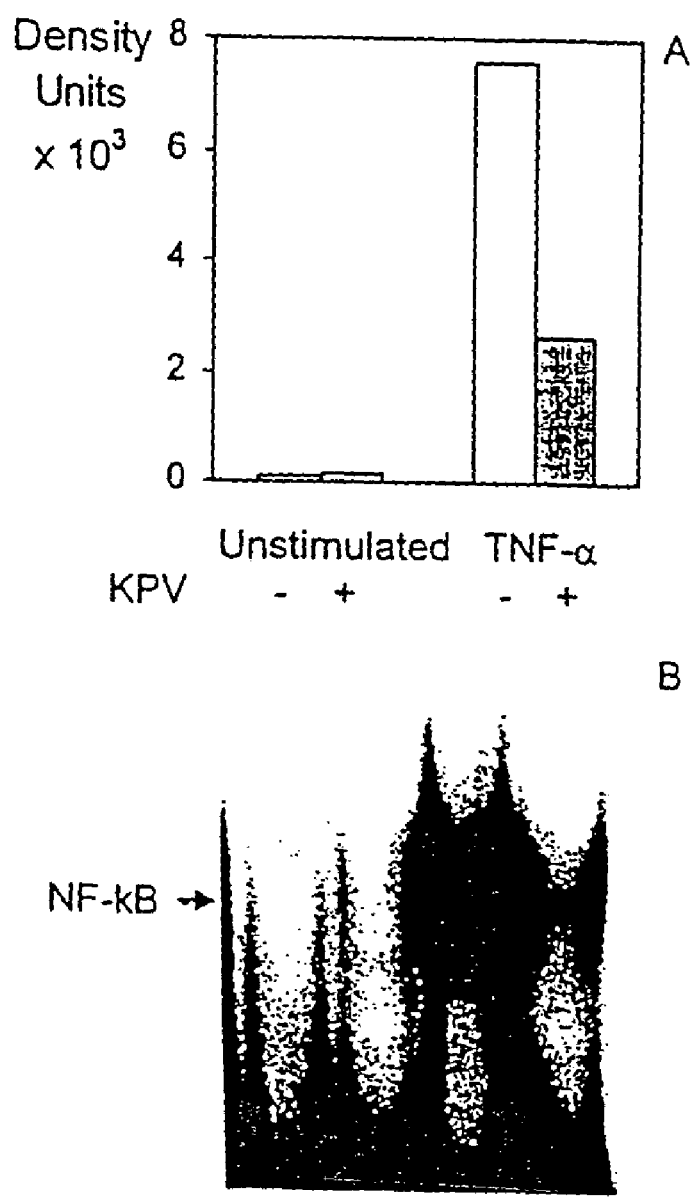
FIG. 14 shows the mechanisms by which alpha-MSH peptides inhibit viral replication, expression and reactivation.

FIG. 14 shows that TNF-α greatly enhanced NF-κB binding activity, but the co-incubation of alpha-MSH (11-13) (SEQ ID NO: 1) at $10^{-5}$ M significantly reduced NF-κB activation. Alpha-MSH (11-13) (SEQ ID NO: 1), however, did not alter NF-κB activation in resting cells. This suggests that alpha-MSH peptides inhibit viral replication and expression through regulation of the NF-κB binding.

Replication of viral agents often depends on the state of activation of infected cells and is often regulated by interactions between viral and host factors. These host factors may include TFN-α and other cytokines such as the interleukins. Similar to HIV-1 infection and activation, herpes simplex virus also becomes reactivated from latency in response to host cytokines. For example, TNF-α and IL-6, but not IL-1 and IL-3, have been shown to reactivate HSV infection. Neutralization of IL-6 with antibody against IL-6 significantly inhibited HSV reactivation while neutralization of interferon alpha and beta did not. See e.g., Baker, M., et. al., *The Relationship between Interleukin-6 and Herpes Simplex Virus Type-1: Implications for Behavior and Immunopathology*, Brain Behav. Immun. 13(3): 201-11 (1999); Noisakran S., e. al., *Lymphocytes Delay Kinetics of HSV-1 Reactivation from in vitro Explants of Latent Infected Trigeminal Ganglia*, J. Neuroimmunol. 95(1-2): 126-35 (1999); Walev, I., et. al., *Enhancement by TNF-alpha of Reactivation and Replication of Latent Herpes Simplex Virus from Trigeminal Ganglia of Mice*, Arch Virol. 140(6): 987-92 (1995); Domk-Optiz, I., et. al., *Stimulation of Macrophages by Endotoxin Results in the Reactivation of a Persistent Herpes Simplex Virus Infection*, Scand J. Immunol. 32(2): 69-75 (1990); Fauci, A. S., *Host Factors in the Pathogenesis of HIV-induced Disease*, Nature 384: 529 (1996).

TNF-α or infection by viruses, including HSV, can cause targeted destruction of IκB, which in turn activates the nuclear translocation of NF-κB. Nuclear translocation promotes NF-κB binding to DNA operators for the transcription of a range of inflammatory agents including TNF-α, IL-6, and other cytokines. The expression of these cytokines, again, further reactivates other HSV infected cells to produce HSV viruses. See e.g., Patel, A., et. al., *Herpes Simplex Type 1 Induction of Persistent NF-κB Nuclear Translocation Increases the Efficiency of Virus Replication*, Virology 247(2): 212-22 (1998).

Thus, by blocking NF-κB binding, alpha-MSH peptides inhibit the expression of more inflammatory cytokines that can reactivate HSV. This example and Examples VII-VIII show that alpha-MSH peptides inhibit viral replication, expression, and reactivation by inhibiting NF-κB binding in response to the body's cytokines or other viral infection.

EXAMPLE X

This example illustrates the ability of alpha-MSH peptides to inhibit viral replication in acutely infected human cells. More specifically, alpha-MSH inhibited the replication and expression of HIV-1 in acutely infected human peripheral blood mononuclear cells (PBMCs).

PBMCs were isolated from normal donors by Ficoll-Hypaque density gradient centrifugation. Monocytes were isolated by Percoll gradient separation and allowed to differentiate into macrophages (MDM) in complete medium of RPMI plus 20% FCS using 24-well tissue culture plates at $10^6$ cells/ml for seven days. MDM were infected with monocytotropic HIVBa-I strain (1:10) overnight. The undiluted viral stock contained $10^7$ infectious units/ml. After 24 hours, MDM were washed and resuspended in complete medium are replaced three times a week, for three weeks. Reverse transcriptase releases were measured weekly post-infection using a commercially available kit, ELISA Retrosys RT assay from Innovagen, Lund, Sweden. $10^{-5}$ M alpha-MSH (11-13) (SEQ ID NO: 1) was added at the time of HIV infection and then daily until harvests.

Figure 15:
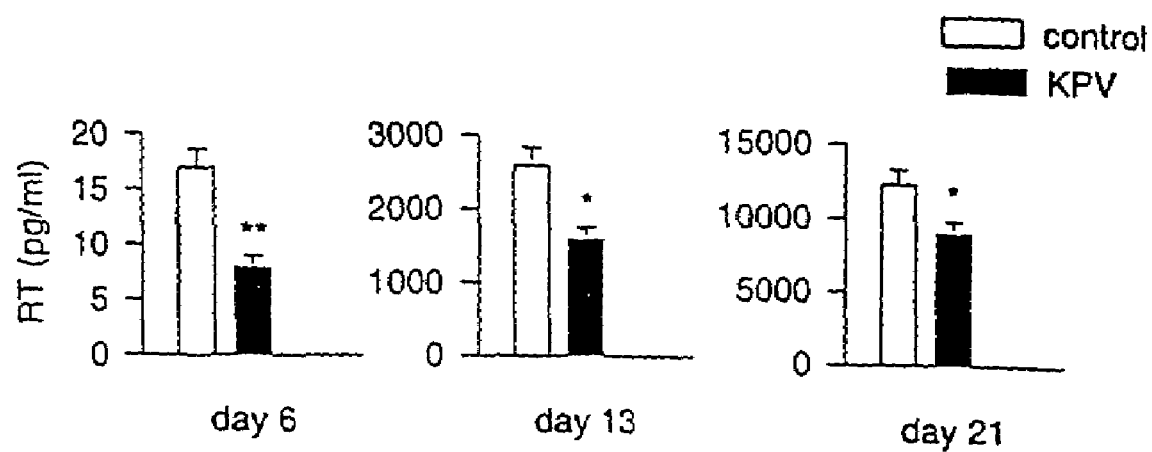
FIG. 15 shows the inhibitory effects of alpha-MSH peptides on viral replication and expression in acutely infected cells.

FIG. 15 shows that alpha-MSH significantly inhibited reverse transcriptase release in acutely infected MDM. This inhibitory effect was more pronounced on day six but was still statistically significant on day 21.

Thus, this example demonstrates that viral replication at the site of infection can be inhibited by alpha-MSH peptides. Consequently, the sexual transmission of venereal diseases in general, and HIV in particular, can be inhibited by associating alpha-MSH peptides with contraceptives such as condoms, diaphragms, or sponges used during sexual contact, and/or the post sexual contact application of suppositories, cream, ointment, gel, or aerosol foams containing alpha-MSH peptides.

EXAMPLE XI

This example illustrates the biological functional equivalents of alpha-MSH peptides.

Although specific amino acid sequences described here are effective, it is clear to those familiar with the art that amino acids can be substituted or deleted without altering the effectiveness of the peptides. Further, it is known that stabilization of the alpha-MSH sequence can greatly increase the activity of the peptide and that substitution of D-amino acid forms for L-forms can improve or decrease the effectiveness of the peptides. For example, a stable analog of alpha-MSH, [Nle$^4$, D-Phe$^7$]-alpha-MSH, which is known to have marked biological activity on melanocytes and melanoma cells, is approximately ten times more potent than the parent peptide in reducing fever. Further, adding amino acids to the C-terminal of alpha-MSH (11-13) (SEQ ID NO: 1) sequence can reduce or enhance antipyretic potency. Addition of glycine to form the 10-13 sequence (SEQ ID NO: 13) slightly decreased potency: the 9-13 sequence (SEQ ID NO: 14) was almost devoid of activity, whereas the potency of the 8-13 sequence (SEQ ID NO: 15) was greater than that of the 11-13 sequence (SEQ ID NO: 1). It is known that Ac-[D-K$_{11}$]-alpha-MSH 11-13-NH$_2$ has the same general potency as the L-form of the tripeptide alpha-MSH (11-13) (SEQ ID NO: 1). Certain references, however, have shown substitution with D-proline in position 12 of the tripeptide rendered it inactive. See e.g., Holdeman. M., et. al., *Antipyretic Activity of a Potent alpha-MSH Analog, Peptides* 6, 273-5 (1985). Deeter, L. B., et. al., *Antipyretic Properties of Centrally Administered alpha-MSH Fragments in the Rabbit, Peptides* 9, 1285-8 (1989). Hiltz, M. E., *Anti-inflammatory Activity of alpha-MSH (11-13) Analogs: Influences of Alterations in Stereochemistry. Peptides* 12, 767-71 (1991).

Biological functional equivalents can also be obtained by substitution of amino acids having similar hydropathic values. Thus, for example, isoleucine and leucine, which have a hydropathic index +4.5 and +3.8, respectively, can be substituted for valine, which has a hydropathic index of +4.2, and still obtain a protein having like biological activity and thus present the opportunity for varying types of KPV dimers. Alternatively, at the other end of the scale, lysine (−3.9) can be substituted for arginine (−4.5), and so on. In general, it is believed that amino acids can be successfully substituted where such amino acid has a hydropathic score of within about +/−1 hydropathic index unit of the replaced amino acid.

EXAMPLE XII

*C. albicans, C. glabrata*. and *C. krusei* (clinical isolates) were obtained from the collection of the laboratory of Microbiology, Ospedale Maggiore di Milano. Six different isolates for each yeast strain were used. *Candida* Sp. cells were maintained on Sabouraud's agar slants and periodically transferred to Sabouraud's agar plates and incubated for 48 h at 28° C. To prepare stationary growth phase yeast, a colony was taken from the agar plates and transferred into 5 ml Sabouraud-dextrose broth and incubated for 48 h at 32° C. Cells were centrifuged at 1,000×g for 10 minutes and the pellet was washed twice with distilled water. Cells were counted and suspended in distilled water to obtain $10^7$ yeast cells/ml. Viability, determined by the exclusion of 0.01% methylene blue, remained >98%.

Tubes containing *Candida* Sp. cells, 1×10$^6$ in 100 μl distilled water, were additioned with the CKPV dimer $10^{-7}$ to $10^{-4}$ M or KPV $10^{-4}$ M (final concentrations) dissolved in 100 μl distilled water. Control tubes received 100 μl of distilled water. All the tests were run in triplicate. After 2 h incubation at 37° C., yeast suspension from each vial was diluted with distilled water to obtain approximately 100 organisms/ml. One milliliter aliquots from each tube were dispensed on blood agar plates and incubated for 48 h at 37° C. to count CFUs. Organism viability was estimated from the number of CFUs in each plate. Only experiments in which CFUs in control plates were between 80 and 120 with a variability in counts less than 10% were used to evaluate effects of the peptides. Experiments with smaller or greater numbers of colonies in control plates were considered technically inappropriate and excluded from analysis.

Figure 17:
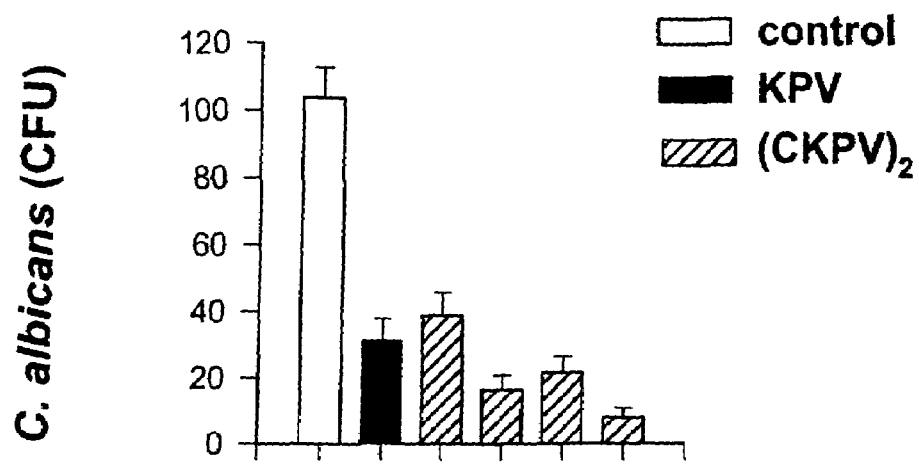
FIG. 17 shows that at the same molarity a KPV dimer (the CKPV dimer) is more than twice as effective as the KPV monomer in treating *C. albicans*.
Figure 18:
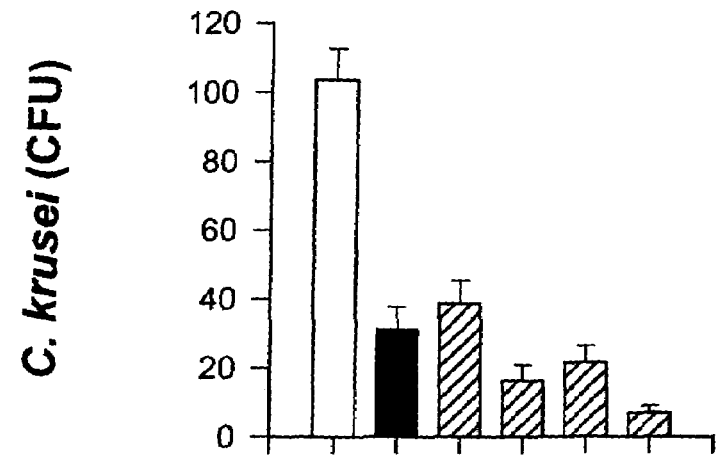
FIG. 18 shows that at the same molarity a KPV dimer (the CKPV dimer) is more than twice as effective as the KPV monomer in treating *C. krusei*.
Figure 19:
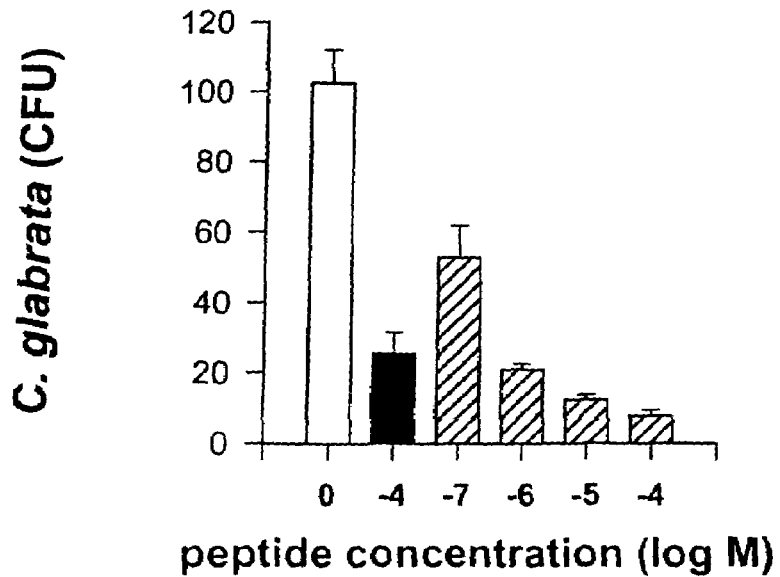
FIG. 19 shows that at the same molarity a KPV dimer (the CKPV dimer) is more than twice as effective as a KPV monomer in treating *C. glabrata*.

Results illustrated in FIGS. 17-19 and show the resulting CFUs under the conditions described above for the particular fungus identified. The figures include the resulting CFUs in the presence of no alpha-MSH peptides (designated as "0" in FIGS. 17-19), $10^{-4}$ M of KPV [designated as "−4" in FIGS. 17-19], $10^{-7}$ M of the CKPV (SEQ ID NO: 5) dimer [designated as "−7" in FIGS. 17-19], $10^{-6}$ M of the CKPV (SEQ ID NO: 5) dimer [designated as "−6" in FIGS. 1-3], $10^{-5}$ M of the CKPV (SEQ ID NO: 5) dimer [designated as "−5" in FIGS. 17 -19], and $10^{-4}$ M of the CKPV (SEQ ID NO: 5) dimer [designated as "−4" in FIGS. 17-19]. FIG. 17 shows that at the same molarity, the CKPV (SEQ ID NO: 5) dimer is more than twice as effective as the KPV monomer in treating *C. albicans*. FIG. 18 shows that at the same molarity, the CKPV (SEQ ID NO: 5) dimer is more than twice as effective as the KPV monomer in treating *C. krusei*. FIG. 19 shows that at the same molarity the CKPV (SEQ ID NO: 5) dimer is more than twice as effective as the KPV monomer in treating *C. glabrata*.

Results illustrated in FIGS. 17-19 and show the resulting CFUs under the conditions described above for the particular fungus identified. The figures include the resulting CFUs in the presence of no alpha-MSH peptides (designated as "0" in FIGS. 17-19). $10^{-4}$ M of KPV [designated as "−4" in FIGS. 17-19], $10^{-7}$ M of the CKPV (SEQ ID NO: 5) dimer [designated as "−7" in FIGS. 17-19], $10^{-6}$ M of the CKPV dimer [designated as "−6" in FIGS. 1-3]. $10^{-5}$ M of the CKPV (SEQ ID NO: 5) dimer [designated as "−5" in FIGS. 17-19]. and $10^{-4}$ M of the CKPV (SEQ ID NO: 5) dimer [desianated as "−4" in FIGS. 17-19]. FIG. 17 shows that at the same motarity, the CKPV (SEQ ID NO: 5) dimer is more than twice as effective as the KPV monomer in treating *C. albicans*. FIG. 18 shows that at the same molarity. the CKPV (SEQ ID NO: 5) dimer is more than twice as effective as the KPV monomer in treating *C. krusei*. FIG. 19 shows that at the same molarity the CKPV (SEQ ID NO: 5) dimer is more than twice as effective as the KPV monomer in treating *C. glabrata*.

The preceding Examples I-XII demonstrate the anti-infection activities and uses of alpha-MSH peptides. These data are intended only as examples and are not intended to limit the invention to these examples. It is understood that modifying the examples above does not depart from the spirit of the invention. It is further understood that the examples can be applied on their own or in combination with each other.

The invention claimed is:

1. A pharmaceutical composition comprising a KPV dimer, a first preservative agent, a solvent, an alkalizer, an acrylic acid-based polymer, a second preservative agent and a gelatinizing agent.

2. The composition of claim 1 further comprising a chelating agent.

3. The composition of claim 1 wherein the KPV dimer is CKPV (SEQ ID NO: 5) dimer.

4. The composition of claim 1 wherein the acrylic acid-based polymer is a high molecular weight, cross-linked, acrylic acid-based polymer.

5. The composition of claim 1 wherein the first preservative is selected from the group consisting of phenoxyethanol, methylparaben, butylparaben, ethylparaben propylparaben and potassium sorbate and combinations thereof.

6. The composition of claim 1 wherein the second preservative is selected from the group consisting of phenoxyethanol, methylparaben, butylparaben, ethylparaben propylparaben and potassium sorbate and combinations thereof.

7. The composition of claim 5 wherein the first preservative is methylparaben.

8. The composition of claim 6 wherein the second preservative is propylparaben.

9. The composition of claim 1 wherein the solvent is selected from the groups consisting of propylene glycol, ethanol, phenol, acetone, glycerol and isopropanol and combinations thereof.

10. The composition of claim 9 wherein the solvent is propylene glycol.

11. The composition of claim 2 wherein the chelating agent is selected from the group consisting of Coenzyme Q10, Zinc, L-Cysteine, L-Methionine, L-Lysine, Glutathione and EDTA and combinations thereof.

12. The composition of claim 11 wherein the chelating agent is EDTA.

13. The composition of claim 1 wherein the alkalizer is selected from the group consisting of HEPES, 2 M NaOH, MES hydrate, MOPS, TAPS and Bis-Tris and combinations thereof.

14. The composition of claim 13 wherein the alkalizer is NaOH.

15. The composition of claim 1 wherein the gelatinizing agent is selected from the group consisting of water, sterile water, distilled water, sterile saline and sterile water for injection and combinations thereof.

16. The composition of claim 15 wherein the gelatinizing agent is sterile water for injection.

17. The composition of claim 3 wherein the CKPV (SEQ ID NO: 5) dimer is at least about 0.05-0.15% of the composition.

18. The composition of claim 17 wherein the CKPV (SEQ ID NO: 5) dimer at least about 0.1% of the composition.

19. The composition of claim 4 wherein the high molecular weight, cross-linked, acrylic acid-based polymer is at least about 1.5-2.5% of the composition.

20. The composition of claim 19 wherein the high molecular weight, cross-linked, acrylic acid-based polymer is at least about 2% of the composition.

21. The composition of claim 7 wherein the methylparaben is at least about 0.1-0.2% of the composition.

22. The composition of claim 21 wherein the methylparaben is at least about 0.15% of the composition.

23. The composition of claim 8 wherein the propylparaben is at least about 0.025-0.075% of the composition.

24. The composition of claim 23 wherein the propylparaben is at least about 0.05% of the composition.

25. The composition of claim 10 wherein the propylene glycol is at least about 5-15% of the composition.

26. The composition of claim 25 wherein the propylene glycol is at least about 10% of the composition.

27. The composition of claim 12 wherein the EDTA is at least about 0.05-0.15% of the composition.

28. The composition of claim 27 wherein the EDTA is at least about 0.1% of the composition.

29. The composition of claim 14 wherein the 2 M NaOH is that quantity sufficient to bring the composition to a pH of 4.0.+−.0.1.

30. The composition of claim 15 wherein the sterile water for injection is that quantity sufficient to create a gel.

31. A pharmaceutical composition comprising a high molecular weight, cross-linked, acrylic acid-based polymer, propylparaben, methylparaben, propylene glycol, CKPV (SEQ ID NO: 5) dimer, 2 M NaOH and sterile water for injection.

32. The composition of claim 31 further comprising EDTA.

33. The composition of claim 31 wherein the CKPV (SEQ ID NO: 5) dimer is at least about 0.1% of the composition.

34. The composition of claim 31 wherein the high molecular weight, cross-linked, acrylic acid-based polymer is at least about 2% of the composition.

35. The composition of claim 31 wherein the methylparaben is at least about 0.15% of the composition.

36. The composition of claim 31 wherein the propylparaben is at least 0.05% of the composition.

37. The composition of claim 31 wherein the propylene glycol is at least about 10% of the composition.

38. The composition of claim 32 wherein the EDTA is at least about 0.1% of the composition.

39. The composition of claim 31 wherein the 2 M NaOH is that quantity sufficient to bring the composition to a pH of 4.0.+−0.1.

40. The composition of claim 31 wherein the sterile water for injection is that quantity sufficient to create a gel.

41. A pharmaceutical composition comprising 2% of a high molecular weight, cross-linked, acrylic acid-based polymer, 0.05% of propylparaben, 0.15% of methylparaben, 10% of propylene glycol, 0.1% g of EDTA, 2 M NaOH in a quantity sufficient to bring the composition to a pH of 4.0.+−0.1, 0.1% of CKPV (SEQ ID NO: 5) dimer and sterile water for injection quantity sufficient to create a gel.

42. A method of treating urogenital conditions comprising the use of a pharmaceutical composition comprising at least about 2% of a high molecular weight, cross-linked, acrylic acid-based polymer, at least about 0.05% of propylparaben, at least about 0.15% of methylparaben, at least about 10% of propylene glycol, at least about 0.1% of EDTA, 2 M NaOH in a quantity sufficient to bring the composition to a pH of 4.0.+−0.1, at least about 0.1% of CKPV (SEQ ID NO: 5) dimer and sterile water for injection quantity sufficient to create a gel.

* * * * *